US010940317B2

(12) United States Patent
Shi et al.

(10) Patent No.: US 10,940,317 B2
(45) Date of Patent: Mar. 9, 2021

(54) SYSTEM AND METHOD OF ADJUSTING THE COMPLIANCE VOLTAGE IN A NEUROMODULATION DEVICE

(71) Applicant: Boston Scientific Neuromodulation Corporation, Valencia, CA (US)

(72) Inventors: Jess Weiqian Shi, Porter Ranch, CA (US); Jordi Parramon, Valencia, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 168 days.

(21) Appl. No.: 16/359,583

(22) Filed: Mar. 20, 2019

(65) Prior Publication Data

US 2019/0217101 A1 Jul. 18, 2019

Related U.S. Application Data

(63) Continuation of application No. 15/421,926, filed on Feb. 1, 2017, now Pat. No. 10,307,595, which is a
(Continued)

(51) Int. Cl.
*A61N 1/36* (2006.01)
*A61N 1/05* (2006.01)

(52) U.S. Cl.
CPC ....... *A61N 1/36153* (2013.01); *A61N 1/0534* (2013.01); *A61N 1/3614* (2017.08);
(Continued)

(58) Field of Classification Search
CPC .............. A61N 1/36153; A61N 1/0534; A61N 1/36125; A61N 1/36128; A61N 1/36139; A61N 1/36178
(Continued)

(56) References Cited

U.S. PATENT DOCUMENTS 6,181,996 B1 1/2001 Chou et al.
6,516,227 B1 2/2003 Meadows et al.
(Continued)

FOREIGN PATENT DOCUMENTS

CN 105722549 A 6/2016
CN 105722549 B 8/2018
(Continued)

OTHER PUBLICATIONS

"U.S. Appl. No. 14/464,557 Decision on Pre-Appeal Brief Request dated Jul. 12, 6", 2 pgs.
(Continued)

*Primary Examiner* — Erin M Piateski
(74) *Attorney, Agent, or Firm* — Schwegman Lundberg & Woessner, P.A.

(57) ABSTRACT

A therapeutic neuromodulation system configured for providing therapy to a patient. The therapeutic neuromodulation system comprises a plurality of electrical terminals configured for being respectively coupled to a plurality of electrodes implanted within tissue, analog output circuitry configured for delivering therapeutic electrical energy between the plurality of electrical terminals in accordance with a set of modulation parameters that includes a defined current value, a voltage regulator configured for supplying an adjustable compliance voltage to the analog output circuitry, and control/processing circuitry configured for automatically performing a compliance voltage calibration process at a compliance voltage adjustment interval by periodically computing an adjusted compliance voltage value as a function of a compliance voltage margin. The control/processing circuitry may also be configured for automatically adjusting at least one of the compliance voltage adjustment interval and the compliance voltage margin during the compliance voltage calibration process.

20 Claims, 13 Drawing Sheets

Related U.S. Application Data continuation of application No. 14/464,557, filed on Aug. 20, 2014, now Pat. No. 9,616,233.

(60) Provisional application No. 61/871,793, filed on Aug. 29, 2013.

(52) U.S. Cl.
CPC ..... *A61N 1/36125* (2013.01); *A61N 1/36128* (2013.01); *A61N 1/36139* (2013.01); *A61N 1/36178* (2013.01)

(58) Field of Classification Search
USPC .......................................................... 607/62
See application file for complete search history.

(56) References Cited

U.S. PATENT DOCUMENTS

| | | | |
|---|---|---|---|
| 6,895,280 B2 | 5/2005 | Meadows et al. | |
| 6,993,384 B2 | 1/2006 | Bradley et al. | |
| 7,539,538 B2 | 5/2009 | Parramon et al. | |
| 7,650,184 B2 | 1/2010 | Walter | |
| 8,019,439 B2 | 9/2011 | Kuzma et al. | |
| 8,175,719 B2 | 5/2012 | Shi | |
| 8,606,362 B2 | 12/2013 | He et al. | |
| 9,616,233 B2 | 4/2017 | Shi et al. | |
| 2003/0139781 A1 | 7/2003 | Bradley et al. | |
| 2005/0267546 A1 | 12/2005 | Parramon et al. | |
| 2007/0038250 A1 | 2/2007 | He et al. | |
| 2007/0135868 A1 | 6/2007 | Shi et al. | |
| 2007/0168004 A1 | 7/2007 | Walter | |
| 2007/0168007 A1 | 7/2007 | Kuzma et al. | |
| 2011/0009927 A1* | 1/2011 | Parker ................ | A61N 1/36139 607/62 |
| 2011/0264171 A1 | 10/2011 | Torgerson | |
| 2013/0073008 A1 | 3/2013 | Ternes et al. | |
| 2013/0116752 A1* | 5/2013 | Parker ................ | A61N 1/36142 607/62 |
| 2015/0066108 A1 | 3/2015 | Shi et al. | |
| 2017/0143974 A1 | 5/2017 | Shi et al. | |

FOREIGN PATENT DOCUMENTS

| | | |
|---|---|---|
| EP | 3038704 B1 | 10/2018 |
| JP | 2009519771 A | 5/2009 |
| JP | 2012532672 A | 12/2012 |
| JP | 2016529039 A | 9/2016 |
| JP | 6280652 B2 | 1/2018 |
| WO | WO-2015031136 A1 | 3/2015 |

OTHER PUBLICATIONS

"U.S. Appl. No. 14/464,557 Pre-Appeal Brief Request filed Jun. 14, 2016", 5 pgs.
"U.S. Appl. No. 14/464,557, Advisory Action dated Jun. 3, 2016", 3 pgs.
"U.S. Appl. No. 14/464,557, Appeal Brief filed Aug. 15, 2016", 49 pgs.
"U.S. Appl. No. 14/464,557, Final Office Action dated Mar. 14, 2016", 17 pgs.
"U.S. Appl. No. 14/464,557, Non Final Office Action dated Aug. 26, 2015", 20 pgs.
"U.S. Appl. No. 14/464,557, Notice of Allowance dated Dec. 2, 2016", 11 pgs.
"U.S. Appl. No. 14/464,557, Preliminary Amendment filed Aug. 20, 2014", 10 pgs.
"U.S. Appl. No. 14/464,557, Response filed Aug. 12, 2016 to Final Office Action dated Mar. 14, 2016", 13 pgs.
"U.S. Appl. No. 14/464,557, Response filed Dec. 21, 2015 to Non Final Office Action dated Aug. 26, 2015", 12 pgs.
"U.S. Appl. No. 15/421,926, Examiner Interview Summary dated Dec. 26, 2018", 3 pgs.
"U.S. Appl. No. 15/421,926, Final Office Action dated Oct. 26, 2018", 12 pgs.
"U.S. Appl. No. 15/421,926, Non Final Office Action dated Feb. 22, 2018", 10 pgs.
"U.S. Appl. No. 15/421,926, Notice of Allowance dated Jan. 23, 2019", 9 pgs.
"U.S. Appl. No. 15/421,926, Response filed Jan. 31, 2018 to Restriction Requirement dated Dec. 5, 2017", 6 pgs.
"U.S. Appl. No. 15/421,926, Response filed Dec. 26, 2018 sto Final Office Action dated Oct. 26, 2018", 9 pgs.
"U.S. Appl. No. 15/421,926, Restriction Requirement dated Dec. 5, 2017", 9 pgs.
"Australian Application Serial No. 2014311594, First Examiners Report dated Oct. 4, 2016", 3 pgs.
"Australian Application Serial No. 2014311594, Response filed Aug. 10, 2017 to First Examiners Report dated Oct. 4, 2016", 11 pgs.
"Australian Application Serial No. 2014311594, Response filed Sep. 28, 2017 to Subsequent Examiners Report dated Aug. 21, 2017", 5 pgs.
"Australian Application Serial No. 2014311594, Subsequent Examiners Report dated Aug. 21, 2017", 4 pgs.
"Australian Application Serial No. 2014311594, Subsequent Examiners Report dated Oct. 3, 2017", 4 pgs.
"Chinese Application Serial No. 201480059143.8, Examiner Interview Summary dated Apr. 18, 2018", English summary from agent, no "official" communication to include, 1.
"Chinese Application Serial No. 201480059143.8, Office Action dated Jan. 16, 2018", w/ English translation, 6 pgs.
"Chinese Application Serial No. 201480059143.8, Office Action dated May 4, 2017", w/ English translation, 27 pgs.
"Chinese Application Serial No. 201480059143.8, Response filed Mar. 1, 2018 to Office Action dated Jan. 16, 2018", w/ claims in English, 16 pgs.
"Chinese Application Serial No. 201480059143.8, Response filed Apr. 20, 2018 to Examiner Interview Summary dated Apr. 18, 2018", w/ English claims, 15 pgs.
"Chinese Application Serial No. 201480059143.8, Response filed Sep. 14, 2017 to Office Action dated May 4, 2017", w/ claims in English, 23 pgs.
"European Application Serial No. 14758252.2, Communication Pursuant to Article 94(3) EPC dated Mar. 23, 2017", 3 pgs.
"European Application Serial No. 14758252.2, Response filed Aug. 2, 2017 to Communication Pursuant to Article 94(3) EPC dated Mar. 23, 2017", 3 pgs.
"International Application Serial No. PCT/US2014/051941, International Preliminary Report on Patentability dated Mar. 10, 2016", 9 pgs.
"International Application Serial No. PCT/US2014/051941, International Search Report dated Nov. 5, 2014", 4 pgs.
"International Application Serial No. PCT/US2014/051941, Written Opinion dated Nov. 5, 2014", 7 pgs.
"Japanese Application Serial No. 2016-538973, Office Action dated Apr. 24, 2017", w/ English translation, 24 pgs.
"Japanese Application Serial No. 2016-538973, Office Action dated Oct. 2, 2017", W/ English Translation, 5 pgs.
"Japanese Application Serial No. 2016-538973, Response filed Jul. 21, 2017 to Office Action dated Apr. 24, 2017", w/ claims in English, 19 pgs.
"Japanese Application Serial No. 2016-538973, Response filed Dec. 18, 2017 to Office Action dated Oct. 2, 2017", w/ claims in English, 13 pgs.

* cited by examiner

| | Period 1 | Period 2 | Period 3a | Period 3b |
|---|---|---|---|---|
| Compliance Voltage Margin | 10% | 5% | 3% | 2% |
| Compliance Voltage adjustment interval | 1 minute | 5 minutes | 4 hours | 24 hours |
| State of tissue voltage drops during period | Difference of short-term tissue voltage drops is greater than Short-term Threshold Value 1 | Difference of short-term tissue voltage drops is equal to or less than Short-term Threshold Value 1 and greater than Short-term Threshold Value 2 | Difference of short-term tissue voltage drops is equal to or less than Short-term Threshold Value 2 and difference of long-term tissue voltage drop is greater than Long-term Threshold Value 1 | Difference of long-term tissue voltage drops is equal to or less than Long-term Threshold Value 1 |

FIG. 8

SYSTEM AND METHOD OF ADJUSTING THE COMPLIANCE VOLTAGE IN A NEUROMODULATION DEVICE

CLAIM OF PRIORITY

The present application is a continuation of U.S. application Ser. No. 15/421,926, filed Feb. 1, 2017, now U.S. Pat. No. 10,307,595, issued Jun. 4, 2019, which is a continuation of U.S. application Ser. No. 14/464,557, filed Aug. 20, 2014, now U.S. Pat. No. 9,616,233, issued Apr. 11, 2017, which claims the benefit under 35 U.S.C. § 119 to U.S. provisional patent application Ser. No. 61/871,793, filed Aug. 29, 2013. The foregoing applications are hereby incorporated by reference into the present application in their entirety.

FIELD OF THE INVENTION

The present inventions relate to tissue modulation systems, and more particularly, to programmable neuromodulation systems.

BACKGROUND

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems have been applied to restore some functionality to paralyzed extremities in spinal cord injury patients.

Each of these implantable neuromodulation systems typically includes at least one neuromodulation lead implanted at the desired modulation site and an neuromodulation device, such as an implantable pulse generator (IPG), implanted remotely from the modulation site, but coupled either directly to the neuromodulation lead(s), or indirectly to the neuromodulation lead(s) via one or more lead extensions. Thus, electrical pulses can be delivered from the neuromodulation device to the electrodes carried by the neuromodulation lead(s) to modulate a volume of tissue in accordance with a set of modulation parameters and provide the desired efficacious therapy to the patient. The neuromodulation system may further comprise a handheld remote control (RC) to remotely instruct the neuromodulator to generate electrical modulation pulses in accordance with selected modulation parameters. The RC may, itself, be programmed by a technician attending the patient, for example, by using a Clinician's Programmer (CP), which typically includes a general purpose computer, such as a laptop, with a programming software package installed thereon.

Electrical modulation energy may be delivered from the neuromodulation device to the electrodes in the form of an electrical pulsed waveform. Thus, electrical modulation energy may be controllably delivered to the electrodes to modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses provided through the electrode array. Each electrode configuration, along with the electrical pulse parameters, can be referred to as a "modulation parameter set."

With some neuromodulation systems, and in particular, those with independently controlled current or voltage sources, the distribution of the therapeutic electrical current between the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

More pertinent to the present inventions, a neuromodulation device may include one or more current sources/sinks that are configured to supply/receive therapeutic electrical current to/from the electrodes. For example, as shown in FIG. 1, a basic output current source 1 and a corresponding output current sink 2 used to deliver electrical energy to tissue exemplified generically as a load resistance R will be described. The output current source 1 includes a current generator 3, digital-to-analog circuitry (DAC) 4, and a selection transistor 5. Likewise, the output current sink 2 includes a current generator 6, a DAC 7, and a selection transistor 8.

Each of the current generators 3, 6 includes transistors M1, M3 each configured for generating a reference current $I_{ref}$. Each of the DACs 4, 7 is configured for scaling the reference current $I_{ref}$ using a parallel number N of transistors M2, M4. It should be appreciated that each of the transistors M1/M3 and transistors M2/M4 can be considered current mirrors. The transistors M1, M3 in the output current source 1 are P-type transistors, and thus, the DAC 4 can be considered a PDAC, and similarly, the output current source 1 can be considered PDAC circuitry. In contrast, the transistors M2, M4 in the output current sink 2 are N-type transistors, and thus, the DAC 7 can be considered an NDAC, and similarly, the output current sink 2 can be considered NDAC circuitry. Without a full discussion of transistor physics, one skilled in the art will recognize that use of transistors of such polarities is sensible, given that the output current source 1 will be tied to a positive voltage (V+, referred to herein as the "compliance voltage"), while the output current sink 2 will be tied to a more negative voltage, such as ground. A "ground voltage" as used herein should be understood as any reference voltage with respect to the compliance voltage.

Each of the selection transistors 5, 8 selects the number of output stages M2, M4 to be activated in the respective DACs 4, 7 in response to the input of a digital signal. Therefore, the DAC 4 may scale the reference current $I_{ref}$ by the selected number j to source an output current $I_{out}$ equal to $j*I_{ref}$ to electrode $E_x$, and the DAC 7 may scale a selection transistor 5 by the selected number k to sink an input current $I_{in}$ equal to $k*I_{ref}$ from electrode $E_y$. Thus, the output current source 1 and output current sink 2 are generally digitally controllable by the selection transistors 5, 8 to respectively generate the output current $I_{out}$ and input current $I_{in}$. If the electrodes $E_x$, $E_y$ are the only electrodes utilized by the neurostimulator, the current $I_{out}$ at $E_x$ will be equal to the current $I_{in}$ at $E_y$. However, as is typical, more than two electrodes may be used, in which case the output current sourced to a particular electrode may not be equal to the output current sunk into another electrode. In any case, the sum of the output current $I_{out}$ sourced by any number of electrodes will be equal to the sum of the input current $I_{in}$ sunk to any number of electrodes As just alluded to, a neuromodulator typically operates with several electrodes, and the various current sources and sinks can be controlled to source or sink current to any particular electrode as is efficacious for treating a particular patient. Different output source/sink architectures can be used in a neuromodulation device. For example, each electrode can be coupled to dedicated PDAC/NDAC circuitry, which allows the electrode to either operate as a current source or a current sink, as described in U.S. Pat. No. 6,181,996, which is expressly incorporated herein by reference. As another example, PDAC/NDAC circuitry can be selectively coupled to any of the electrodes via a low-impedance switching matrix, as described in U.S. Pat. No. 6,516,227, which is expressly incorporated herein by reference. As still another example, instead of using discrete PDAC and NDAC blocks that services the various electrodes, the PDAC and NDAC circuitry is effectively distributed such that any of a number of current mirrors can be coupled to any of the electrodes, as described in U.S. patent application Ser. No. 11/177,503, which is expressly incorporated herein by reference.

Regardless of the current source/sink architectures used, all generally have similar current output path characteristics. That is, referring back to FIG. 1, the current output paths in each architecture comprises, at a minimum, a current source output transistor (or transistors if paralleled for current gain) 3, a selection transistor 5 to control the flow of the current source transistor(s) 3, the load resistance R, a current sink transistor (or transistors if paralleled for current gain) 6, and a selection transistor 7 to control the flow of the current sink transistor(s) 6. Each of these elements has some resistance, and hence some amount of the compliance voltage V+ will be dropped across these elements when current is flowing through the load resistance R. Specifically, the compliance voltage V+ will equal $V_{DS1}+VR+V_{DS2}$, where $V_{DS1}$ is the drain-to-source voltage drop across the current source transistor(s) 3 and the selection transistor 4, and $V_{DS2}$ is the drain-to-source voltage drop across the current sink transistor(s) 6 and the selection transistor 7, and $V_R$ equals the voltage drop across the load resistance R.

It should be appreciated that the M1/M3 and M2/M4 current mirrors require that transistors M1 and M2 operate in saturation mode, such that the channels of the transistors are in "pinch off," as illustrated in FIG. 2. When in the saturation mode, the output current $I_{out}$ is proportional to the gate voltage of the transistors M1 or M2, but does not depend upon the drain voltage to the first order. However, to keep the transistors M1 and M2 in the saturation mode, a certain drain-to-source voltage $V_{DS}$ has to be satisfied for each transistor.

What this means in the context of the output current circuitry of FIG. 1 is that the circuit can operate properly over a range of compliance voltages V+. For example, suppose a suitable therapy for a patient suggests that a current of $I_{out}$=5 mA should be passed between electrodes $E_x$ and $E_y$. Suppose further that the load resistance R equals 800 ohms. When the current of 5 mA is passed through the load resistance R, a voltage $V_R$=4V will build up across the resistance load R (V=I*R). Suppose further for simplicity that the minimum drain-to-source voltage to keep the output transistors M1 and M2 in saturation equals 1V when the effects of the selection transistors 4, 7 are included. The actual value can be different, but is chosen as 1V for ease of illustration. To provide this current, a minimum compliance voltage V+ of at least 6V would be needed; if V+<6V, the circuitry will be unable to produce the desired amount of current.

The compliance voltage V+ could be higher than 6V while still producing the proper amount of current. For example, suppose for the same example that the compliance voltage V+ is 8V. In this case, the circuitry is still capable of providing the 5 mA current, and the load (which doesn't change) will still drop 4V at that current. What this means is that the remainder of the compliance voltage must be dropped across the output transistors M1 and M2 as well as their associated selection transistors 4, 7, e.g., 2V if the source and sink are matched.

However, running the circuit in this example with an 8V compliance voltage is not efficient. While circuit performance is the same at both 6V and 8V, i.e., both are capable of generating a 5 mA current. At 6V, only 30 mW of power (P=I*V) will be drawn, while at 8V, 40 mW of power will be drawn. In other words, 10 mW of power is needlessly dropped across the output transistors M1, M2 and their selection transistors 4, 7. This waste of power is regrettable in the context of an implantable medical device, such as an IPG, which requires a source of energy either supplied by a battery or an external charging source. Therefore, it is important to minimize circuit operation that would otherwise needlessly drain the battery and cause the IPG to cease functioning, or needlessly require the patient to more frequency recharge the battery.

Unfortunately, it is difficult to design the compliance voltage to an optimum level. Depending on the electrodes that are activated, the magnitude of the current required for efficient therapy for a given patient, and the resistance of the patient's flesh, an optimal compliance voltage from the vantage point of power conservation is variable. As such, mechanisms have been designed into prior art neuromodulation systems that adjust the compliance voltage each time the programmed electrical current amplitude or electrode combination is changed by the user. Although the compliance voltage can theoretically be adjusted at a rapid rate (e.g., every minute) to compensate for potential changes in the tissue environment, thereby ensuring that the current source/sink circuitry continues to function properly to provide the current at the programmed amplitude in response to these tissue impedance changes, the compliance voltage adjustment requires bursts of high power drain, and may consume significant amounts of energy. Thus, performing too many compliance voltage adjustments will waste energy. In extreme cases, constant compliance voltage adjustments not only creates high system power consumption, but also prevents the IPG from performing other tasks. As such, a fixed compliance voltage margin (e.g., 12%) is built into the adjusted compliance voltage to ensure that the delivered therapy is not compromised without having to continually make compliance voltage adjustments.

This compliance voltage margin, of course, represents wasted energy, and if the tissue environment has stabilized over a period of time, the compliance margin may be unnecessarily too large. Furthermore, in the context of some therapeutic applications, such as SCS, the change in the tissue impedance is rather slow relative to the frequency at which the amplitude and/or electrode combination, and thus the compliance voltage, is adjusted. As such, a moderate compliance voltage margin, such 12%, will be sufficient to compensate for the tissue impedance changes between compliance voltage adjustments.

However, in other therapeutic applications, such as DBS, it has been discovered that the impedance of the tissue (in the case of DBS, brain tissue) varies greatly over both the long term and the short term. In particular, there have been a number of DBS impedance data sets from animal trials and limited human experiments suggesting that brain tissue impedance tends to vary significantly during both the long term and short term.

For example, it has been demonstrated that the tissue impedance of brain tissue measured from a neuromodulation lead rapidly increases during the first four weeks of implantation (in this case, about 40%), gradually decreases during the next eight weeks after implantation (in this case, about −40%), and then stabilizes thereafter, as shown in FIG. 3. If the compliance voltage is left unchanged after implantation, the therapy will be significantly compromised (under compliance) two weeks after implantation until the impedance subsequently drops to a level where the compliance voltage is sufficient. Even if the amplitude and/or electrode combination, and thus the compliance voltage, is adjusted at least one time during this period, thereby at least partially compensating for the change in impedance over the long term, the compliance voltage margin, which translates to a higher compliance voltage, will be relatively large when the tissue impedance stabilizes, thereby unnecessarily wasting energy.

It has also been demonstrated that the tissue impedance of brain tissue measured from a neuromodulation lead rapidly increases from a baseline level to a peak during the first ten minutes of electrical energy delivery (in this case, about 30%), rapidly decreases during the next ten minutes of electrical energy delivery (in this case, about −30%), gradually decreases during the next forty minutes (in this case, about −15%), and then stabilizes thereafter, as shown in FIG. 4. Because it is unlikely that the amplitude value or electrode combination would be adjusted during the initial sixty minute period of therapy, or at least at the rate at which compliance voltage adjustments can effectively compensate for the impedance changes, the therapy will be significantly compromised during the first twenty minutes (during the rapid increase of the tissue impedance to the peak, and the rapid decrease of the tissue impedance to the baseline level) and will considerably waste energy for the remainder of the therapy session (during the gradual decrease of the tissue impedance from the baseline level).

It can be appreciated from the foregoing that an improved technique for effectively and efficiently adjusting the compliance voltage of a neuromodulation device designed to deliver a constant current is needed.

SUMMARY OF THE INVENTION

In accordance with a first aspect of the present inventions, a therapeutic neuromodulation system is provided. The neuromodulation system comprises a plurality of electrical terminals configured for being respectively coupled to a plurality of electrodes implanted within tissue, analog output circuitry configured for delivering therapeutic electrical energy (e.g., an electrical pulse train) between the plurality of electrical terminals in accordance with a set of modulation parameters that includes a defined current value (e.g., a user-programmed value), and a voltage regulator configured for supplying an adjustable compliance voltage to the analog output circuitry. The neuromodulation system optionally comprises a battery to which the voltage regulator is coupled.

In one embodiment, the analog output circuitry comprises a current source and/or current sink configured for delivering the therapeutic electrical energy between the electrical terminals. The neuromodulation system may further comprise a plurality of coupling capacitors respectively coupled to the plurality of electrical terminals, in which case, the current source and/or the current sink may be configured for delivering therapeutic electrical energy between the plurality of electrical terminals via the capacitors.

The neuromodulation system further comprises control/processing circuitry configured for automatically performing a compliance voltage calibration process at a compliance voltage adjustment interval by periodically computing an adjusted compliance voltage value as a function of a compliance voltage margin, and directing the voltage regulator to adjust the compliance voltage to the adjusted compliance voltage value. The compliance voltage calibration process may be performed when the analog output circuitry delivers the therapeutic electrical energy between the plurality of electrical terminals over a continuous therapeutic period without changing the set of modulation parameters. The compliance voltage calibration process may be initiated each time the delivery of the electrical energy by the analog output circuitry is initiated in accordance with the unchanged set of modulation parameters.

The neuromodulation system may further comprise monitoring circuitry configured for measuring a voltage drop (e.g., across the current source and/or current sink, across the capacitors) in the analog output circuitry. In this case, the control/processing circuitry may be configured for computing the adjusted compliance voltage value based on the measured voltage drop. For example, the control/processing circuitry may be configured for computing a voltage drop across the tissue based on a difference between the compliance voltage and the measured voltage drop across the current source and/or current sink. Or, the control/processing circuitry may be configured for computing the voltage drop across the tissue based on a difference between the compliance voltage and a sum of the measured voltage drop across the current source and/or the current sink and the measured voltage drops across the capacitors.

In one embodiment, the control/processing circuitry may be configured for computing the adjusted compliance voltage value as a function of the voltage drop across the tissue and an operating voltage of at least one current source and at least one current sink. The function may be a sum of the voltage drop across the tissue, the operating voltage of at least one current source and at least one current sink, and the compliance voltage. In this case, the compliance voltage margin may be a percentage of the voltage drop across the tissue.

In another embodiment, the control/processing circuitry may be configured for directing the voltage regulator to incrementally vary the compliance voltage to a baseline value that causes the voltage drop across the at least one of the current source and the current sink to meet a threshold value, and computing the adjusted compliance voltage based on the baseline value.

In an optional embodiment, the control/processing circuitry may be further configured for automatically adjusting the compliance voltage adjustment interval and/or compliance voltage margin during the compliance voltage calibration process. The compliance voltage adjustment interval is typically increased over the course of the compliance voltage calibration process. For example, the compliance voltage adjustment interval may be adjusted from a value in the range of 0-20 minutes to a value in the range greater than 20 minutes. Or, the compliance voltage adjustment interval may be adjusted from a value in the range of 20-60 minutes to a value in the range greater than 60 minutes. Or, the compliance voltage adjustment interval may be adjusted from a value in the range of 60 minutes to 1 day in the range greater than 1 day. The compliance voltage margin, which may be a voltage drop percentage, is typically decreased over the course of the compliance voltage calibration process. For example, the voltage drop may be adjusted from a value in the range greater than 10% to a value less than 10%. Or, the voltage drop percentage may be adjusted from a value in the range between 5%-10% to a value less than 2%. Or, the voltage drop percentage may be adjusted from a value in the range of 1%-2% to a value less than 1%.

To automatically make the adjustments to the compliance voltage adjustment intervals and/or compliance voltage margin, the control/processing circuitry may be further configured for periodically directing the monitoring circuitry to measure an electrical parameter data (e.g., voltage drop across at least one component in the analog output circuitry) indicative of change in impedance in the tissue and determining voltage drops (e.g., a voltage drop across the tissue, the compliance voltage) based on the measured electrical parameters.

The control/processing circuitry may be further configured for computing a function of at least two of the determined voltage drops and adjusting the compliance voltage adjustment interval and/or compliance voltage margin based on the computed function. For example, the computed function may be a difference in the voltage drops determined at two consecutive compliance voltage adjustment intervals. Or the computed function may be an average of voltage drop differences determined between a plurality of consecutive compliance voltage adjustment intervals. The control/processing circuitry may be further configured for comparing the computed function to a first threshold value, and adjusting the compliance voltage adjustment interval and/or compliance voltage margin based on the comparison. The compliance voltage adjustment interval and/or compliance voltage margin may be adjusted only if the computed function meets (or drops below) the first threshold value.

Similar to the above, the control/processing circuitry may also be configured for computing another function of at least another two of the voltage drops, and adjusting at least one of the compliance voltage interval and the compliance voltage margin based on the other computed function. The other computed function may be similarly compared to a second threshold value different from the first threshold value. The control/processing circuitry may be further configured for readjusting the compliance voltage adjustment interval and/or compliance voltage margin based on the other comparison. The compliance voltage adjustment interval and/or compliance voltage margin may be readjusted only if the other computed function meets (or drops below) the second threshold value.

In an alternate embodiment, rather than dynamically adjusting the compliance voltage adjustment interval and/or compliance voltage margin based on periodic voltage drop measurements, the control/processing circuitry may be configured for adjusting the at least one of compliance voltage adjustment interval and the compliance voltage margin in accordance with a predetermined time schedule.

The neuromodulation system may further comprise a housing containing the plurality of electrical terminals, the modulation output circuitry, the voltage regulator, and the control/processing circuitry.

In accordance with a second aspect of the present inventions, a neuromodulation system comprises a plurality of electrical terminals configured for being respectively coupled to a plurality of electrodes implanted within tissue, analog output circuitry configured for delivering therapeutic electrical energy between the plurality of electrical terminals in accordance with a set of modulation parameters that includes a defined current value (e.g., a user-programmed value), and a voltage regulator configured for supplying an adjustable compliance voltage to the analog output circuitry. The neuromodulation system further comprises control/processing circuitry configured for performing a compliance voltage calibration process at a compliance voltage adjustment interval by periodically computing an adjusted compliance voltage value as a function of a compliance voltage margin, directing the voltage regulator to adjust the compliance voltage to the adjusted compliance voltage value, and for adjusting at least one of the compliance voltage adjustment interval and the compliance voltage margin during the voltage compliance calibration process.

The compliance voltage adjustments may be automatically performed as described above or manually performed in response to user input. The adjustment of the compliance voltage adjustment interval and/or compliance voltage margin may be performed in the same manner described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a timing diagram illustrating dynamic adjustments of compliance voltage margins and compliance voltage adjustment intervals during a compliance voltage calibration process performed by the DBS system of FIG. 3;

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder subluxation, headache, etc. It should also be appreciated that although the description of the therapy is super-threshold in that the neural tissue is stimulated, it should be appreciated that the invention also lends itself to sub-threshold therapy.

Figure 5:
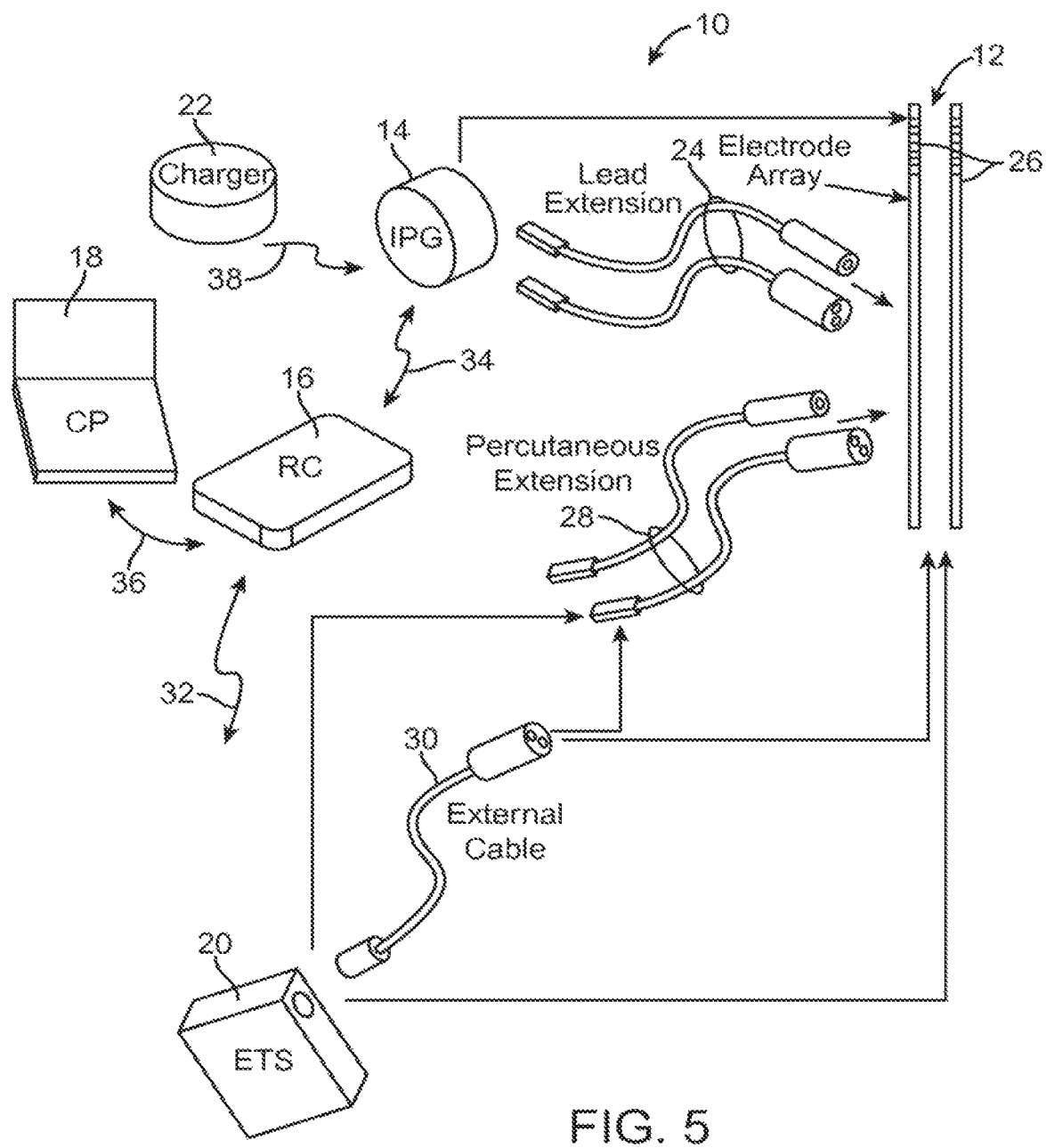
FIG. 5 is a plan view of a DBS system constructed in accordance with one embodiment of the present inventions.

Turning first to FIG. 5, an exemplary DBS system 10 generally includes at least one implantable neuromodulation 12 (in this case, two), a neurostimulator in the form of an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if, e.g., cortical brain stimulation is desired. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters. In this case, the electrical modulation energy is stimulation energy, and the set of modulation parameters is a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETM 20, and external charger 22 will not be described herein. Details of exemplary embodiments of these devices are disclosed in U.S. Pat. No. 6,895,280, which is expressly incorporated herein by reference.

Figure 6:
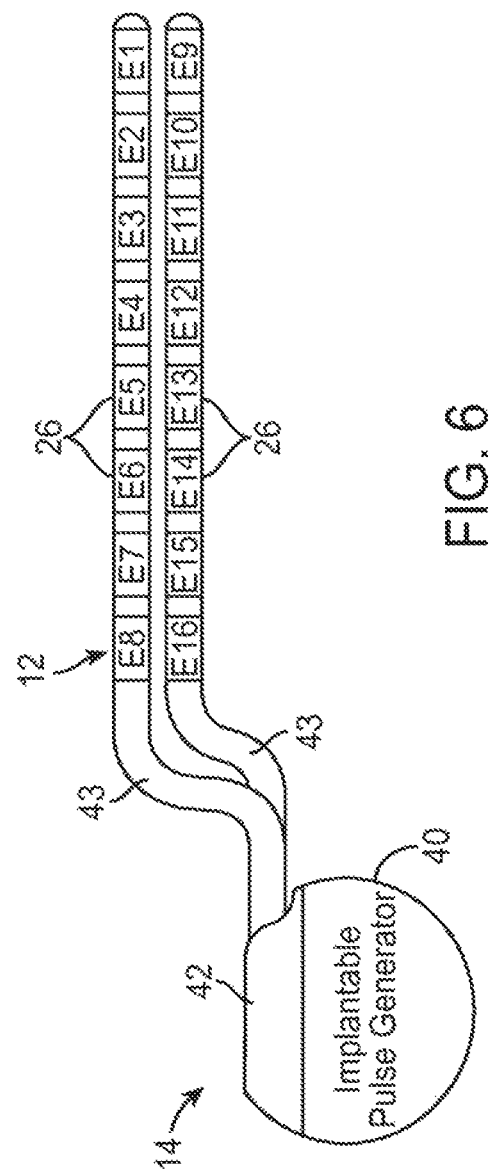
FIG. 6 is a profile view of an implantable pulse generator (IPG) and neuromodulation leads used in the DBS system of FIG. 5.

Referring to FIG. 6, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids, in some cases, the outer case 40 may serve as an electrode.

Each of the neurostimulation leads 12 comprises an elongated cylindrical lead body 43, and the electrodes 26 take the form of ring electrodes mounted around the lead body 43. One of the neurostimulation leads 12 has eight electrodes 26 (labeled E1-E8), and the other neurostimulation lead 12 has eight electrodes 26 (labeled E9-E16). The actual number and shape of leads and electrodes will, of course, vary according to the intended application. In an alternative embodiment, the electrodes 26 take the form of segmented electrodes that are circumferentially and axially disposed about the lead body 43.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the array 22 over multiple channels or over only a single channel.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Multipolar stimulation occurs when at least three of the lead electrodes 26 are activated, e.g., two as anodes and the remaining one as a cathode, or two as cathodes and the remaining one as an anode.

In the illustrated embodiment, IPG 14 can individually control the magnitude of electrical current flowing through each of the electrodes. In this case, it is preferred to use current generators, wherein individual current-regulated amplitudes from independent current sources for each electrode may be selectively generated. While individually programmable electrode amplitudes are optimal to achieve fine control, a single output source switched across electrodes may also be used, although with less fine control in programming. Further details discussing the detailed structure and function of IPGs are described more fully in U.S. Pat. Nos. 6,516,227 and 6,993,384, which are expressly incorporated herein by reference.

Figure 7:
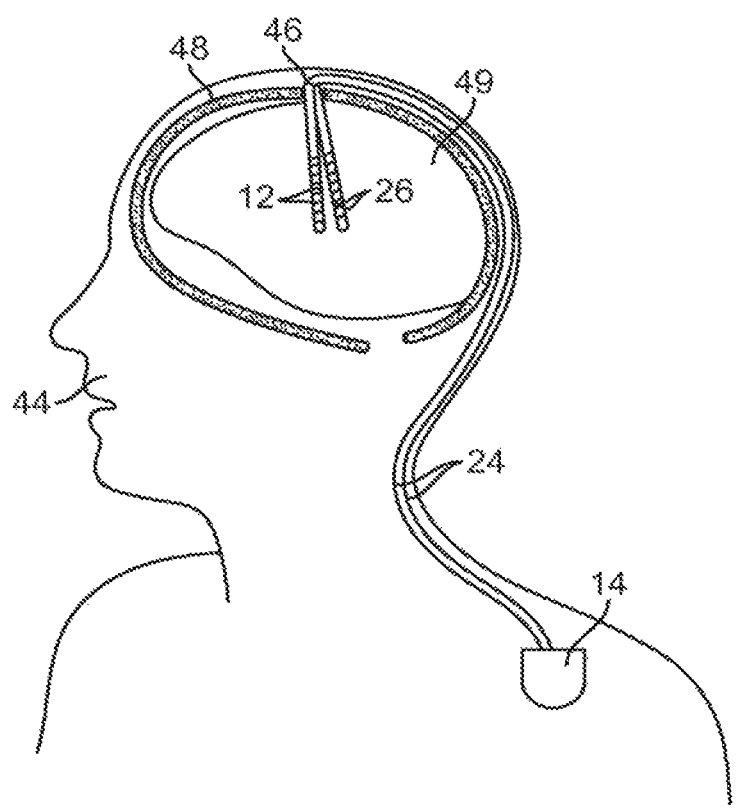
FIG. 7 is a plan view of the DBS system of FIG. 5 in use with a patient.

As shown in FIG. 7, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

More significant to the present inventions, because the patient typically does not feel paresthesia during DBS therapy, the user may not notice an interruption in DBS therapy if the IPG 14 stops functioning due to the highly variable nature of brain tissue impedance. Thus, to ensure that the IPG 14 functions smoothly with sufficient compliance voltage to compensate for the varying tissue impedance, the DBS system 10 (shown in FIG. 5) is configured for automatically making periodic adjustments to the compliance voltage, such that efficacious tissue neuromodulation is maintained without unnecessarily wasting energy. That is, after a compliance voltage calibration process is initiated by the user, the periodic adjustments to the compliance voltage are made without any user intervention.

The compliance voltage calibration process entails making periodic automatic compliance voltage adjustments until the IPG 14 is turned off or a new compliance voltage calibration process is initiated. The compliance voltage calibration process is initiated when electrical energy associated with a set of modulation parameters is delivered to the tissue, and re-initiated whenever there is a change in the set of modulation parameters (e.g., amplitude, pulse width, pulse rate) associated with the delivered electrical energy. In other words, the compliance voltage calibration process is initiated whenever electrical energy having a new set of modulation parameters (e.g., whenever the IPG is turned on or whenever there is a change in the set of modulation parameters) is delivered to the tissue.

Figure 3:
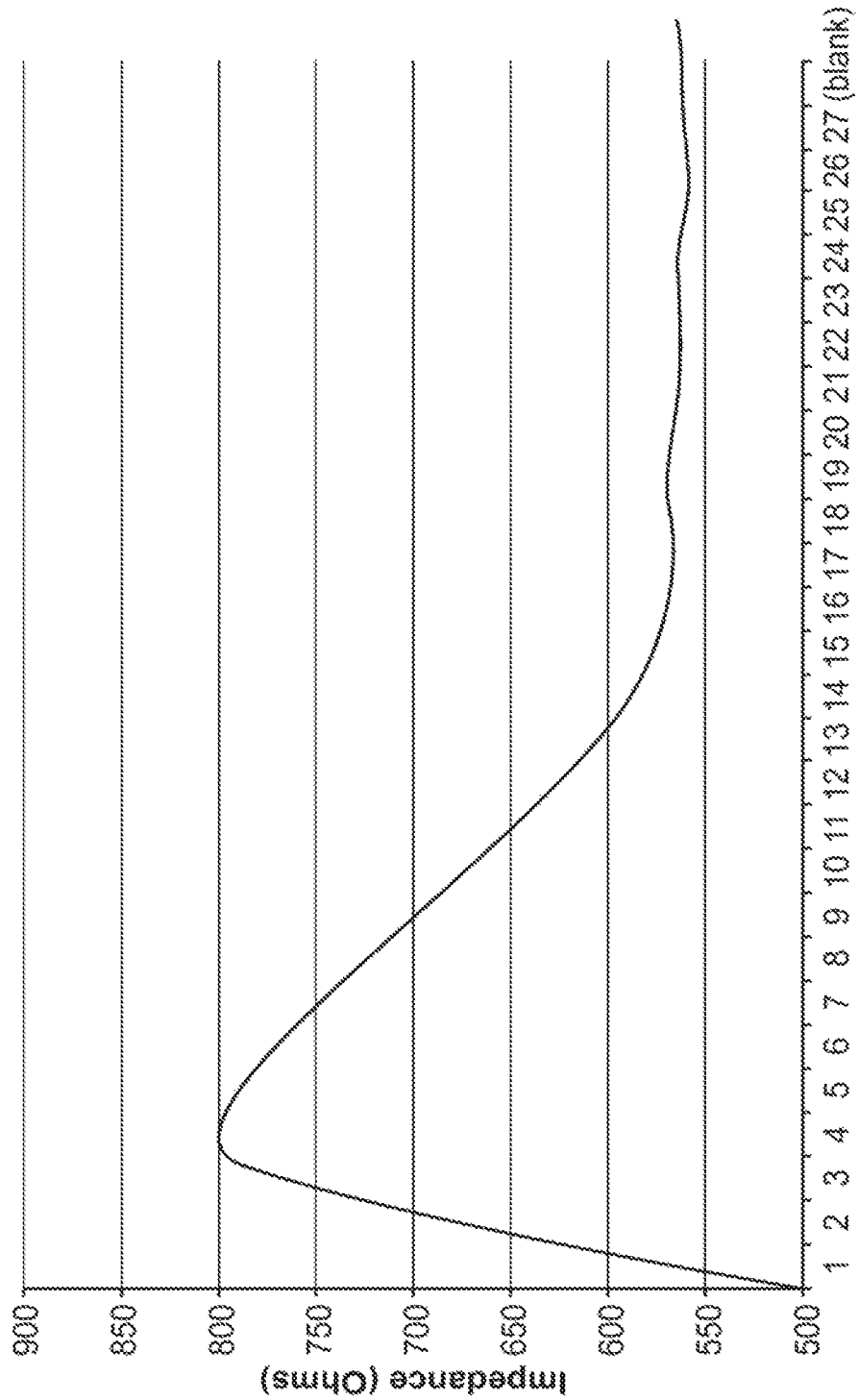
FIG. 3 is a plot of a typical long-term tissue impedance measured by a neuromodulation lead implanted within the brain tissue.

The DBS system 10 is configured for making the periodic automatic compliance voltage adjustments at compliance voltage adjustment intervals. The compliance voltage adjustment interval is the period of time between two consecutive compliance voltage adjustments. After each compliance voltage adjustment interval, the DBS system 10 is configured for computing an adjusted compliance voltage as a function of a compliance voltage margin. The compliance voltage margin compensates for any drastic changes in tissue impedance, on top of a baseline compliance voltage necessary to deliver the programmed electrical current to the tissue. At each compliance voltage adjustment, the DBS system 10 is configured for incorporating an appropriate computed compliance voltage margin into the adjusted compliance voltage in a manner that, prior to the next compliance voltage adjustment, compensates for the varying tissue impedance in the short-term (as shown in FIG. 4) and the long-term (as shown in FIG. 3).

Figure 1:
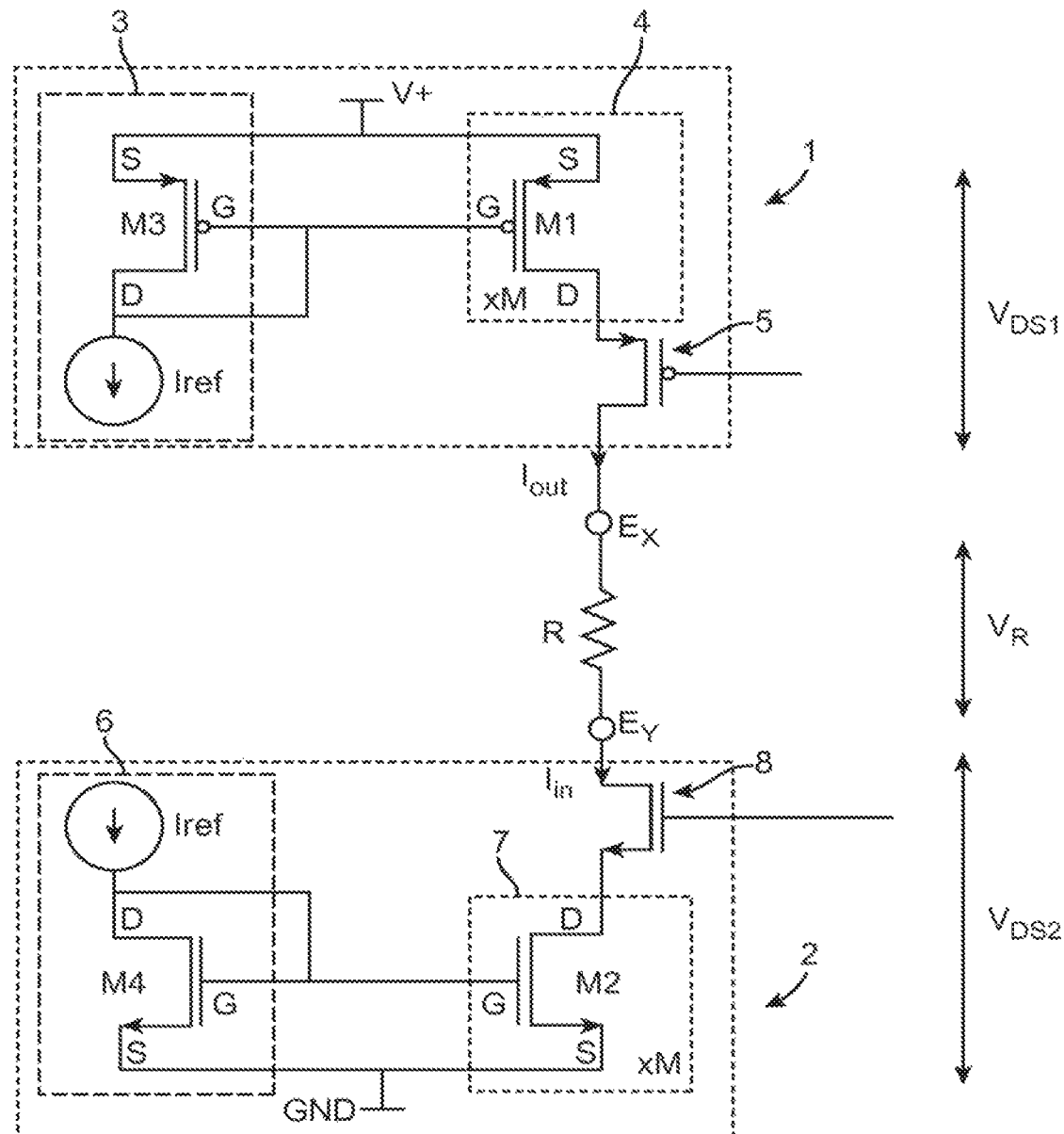
FIG. 1. is a circuit diagram of prior art current source/sink circuitry used in a therapeutic neuromodulation system for delivering current to a tissue load resistance.
Figure 2:
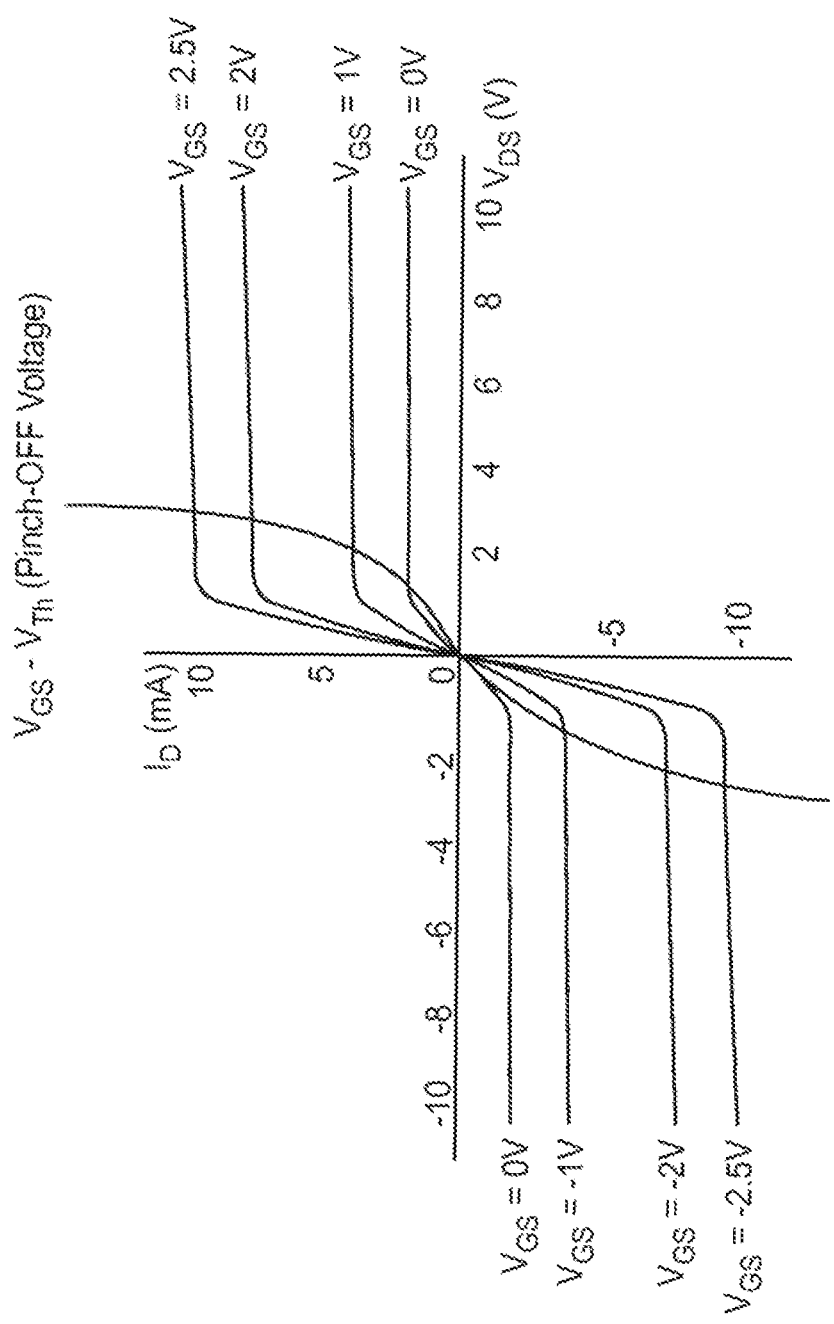
FIG. 2 is a plan view of current and voltage characteristics of field effect transistors used in the prior art current source/sink circuitry of FIG. 1.

In one embodiment, the compliance voltage margin may be a percentage of one or more voltage drops generated by the IPG 14. For example, in the preferred embodiment, the compliance voltage margin may be a percentage of tissue voltage drop $V_R$ across the tissue resistance R (shown in FIG. 1). In another example, the compliance voltage margin may be a percentage of the voltage drop across certain components of the analog output circuitry (described in further detail below with respect to FIG. 11.). Ostensibly, since the tissue voltage drop $V_R$ changes most dramatically as a result of the varying impedance exhibited by the tissue, calculating the compliance voltage margin as a percentage of $V_R$ may prove most efficient. In another embodiment, the compliance voltage margin may simply be a fixed voltage margin.

Significantly, the DBS system 10 is configured to adjust both the compliance voltage margin and the compliance voltage adjustment interval to mirror the underlying changes in tissue impedance while minimizing unnecessary power consumption.

Figure 4:
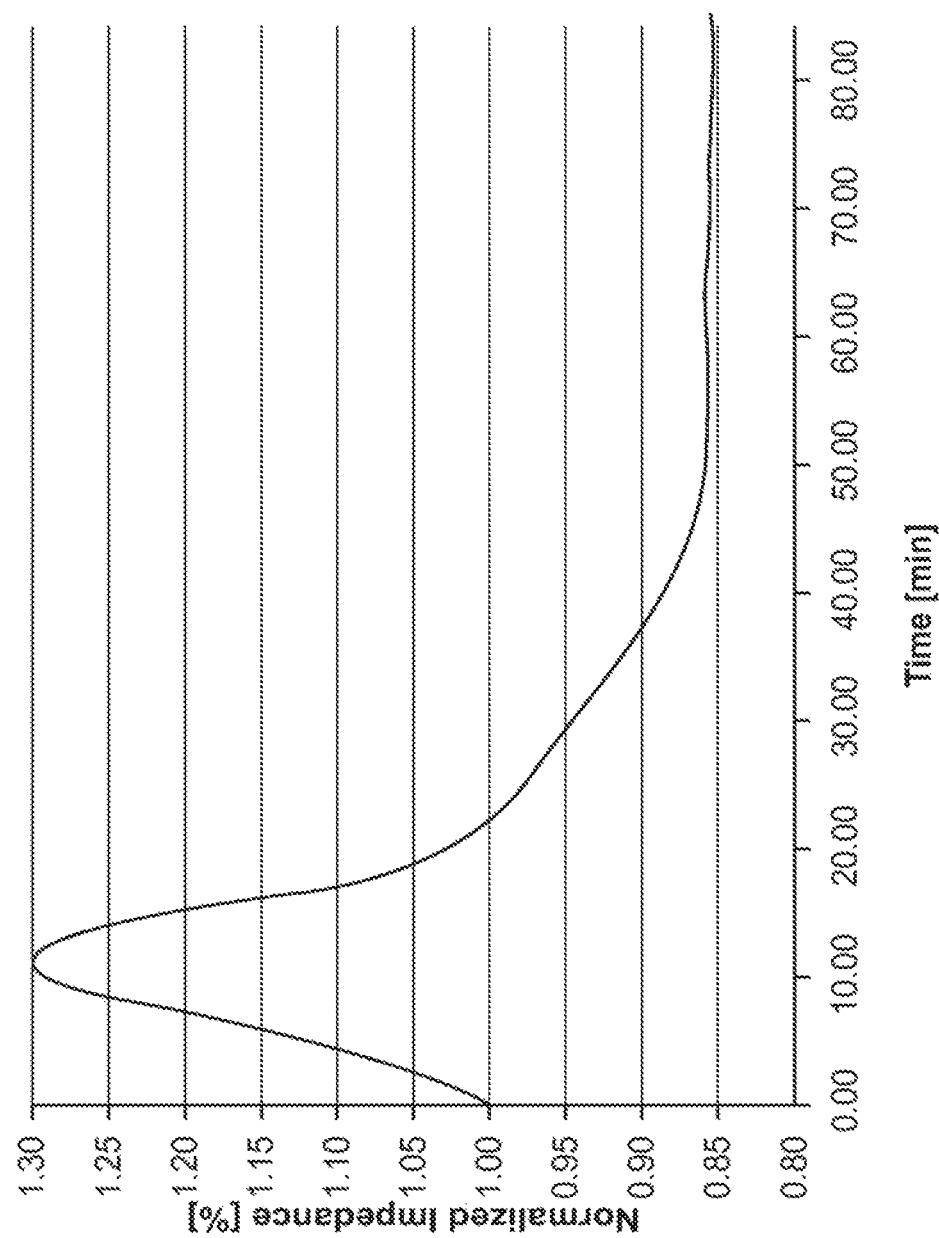
FIG. 4 is a plot of a typical normalized short-term impedance exhibited by tissue measured by an active neuromodulation lead implanted within the brain tissue.

In particular, the DBS system 10 is configured for maintaining a relatively high compliance voltage margin (e.g., 10%), during a first period when the tissue impedance is rapidly fluctuating in the short-term (e.g., the first 20 minutes after the start of tissue modulation in FIG. 4), maintaining a relatively moderate compliance voltage margin (e.g., 5%), during a second period when the tissue impedance is changing at a decreased rate in the short-term (e.g., the next 40 minutes in FIG. 4), and maintaining a relatively low compliance voltage margin (e.g., 2% or 3%), during a third period when the tissue impedance is changing at an even more decreased rate in the short-term (e.g., after an hour in FIG. 4); that is, when the tissue impedance has stabilized.

In a similar vein, the DBS system 10 is configured for maintaining a relatively short compliance voltage adjustment interval (e.g., 1 minute), at which the voltage compliance adjustments are made during the first period when the tissue impedance is rapidly fluctuating in the short-term (e.g., the first 20 minutes after the start of tissue modulation in FIG. 4), maintaining a relatively moderate compliance voltage adjustment interval (e.g., 5 minutes), at which the voltage compliance adjustments are made during the second period when the tissue impedance is changing at a decreased rate in the short-term (e.g., the next 40 minutes in FIG. 4), and maintaining a relatively long compliance voltage adjustment interval (e.g., 4 hours or 24 hours), at which the voltage compliance adjustments are made during the third period when the tissue impedance is changing at an even more decreased rate in the short-term (e.g., after an hour in FIG. 4); that is, when the tissue impedance has stabilized.

It should be appreciated that the DBS system 10 is further configured for adjusting the compliance voltage margin and the compliance voltage adjustment interval to compensate for long-term trends in tissue impedance in addition to the short-term trends in tissue impedance discussed above. In the first 4 weeks after implantation, the tissue impedance is still increasing (as shown in FIG. 3), albeit at a much slower rate when compared to the rapid increase in tissue impedance observed during the first 10 minutes of delivering electrical energy (as shown in FIG. 4). After the first 4 weeks, the tissue impedance steadily decreases until week 15 after which the tissue impedance is mostly stable. While the long-term changes in tissue impedance (as shown in FIG. 3) only occur in the few months immediately after implantation, the short-term changes in tissue impedance resulting from the cycling of the IPG 14 on or the adjustment in the modulation parameters (as shown in FIG. 4) are much more drastic than the long-term changes in tissue impedance. Thus, the DBS system 10 essentially compensates for short-term tissue impedance changes over the course of the first and second periods. However, the long-term changes in tissue impedance may be greater than the stabilized short-term tissue impedance during the third period, and thus, the compliance voltage margin and/or the compliance voltage adjustment may be adjusted differently at the third period based on when (in the course of time after implantation) the compliance voltage calibration process is initiated.

In particular, during the third period, after the short-term impedance has stabilized, the DBS system 10 is configured for maintaining a relatively low compliance voltage margin (e.g., 3%), when the long-term impedance has not yet completely stabilized (e.g., the first 4 weeks after implantation in FIG. 3) and maintaining a minimally low compliance voltage margin (e.g., 2%), when the long-term impedance is decreasing slowly or has stabilized (e.g., after the first 4 weeks in FIG. 3). Similarly, during the third period, after the short-term impedance has stabilized, the DBS system 10 is configured for maintaining relatively long compliance voltage adjustment intervals (e.g., 4 hours), when the long-term impedance has not yet completely stabilized (e.g., the first 4 weeks after implantation in FIG. 3) and maintaining very long compliance voltage adjustment intervals (e.g., 24 hours), during the third period when the long-term impedance is decreasing slowly or has stabilized (e.g., after the first 4 weeks in FIG. 3).

It should be appreciated that adjustments made to the compliance voltage margins and/or compliance voltage adjustment intervals in the first and second periods will be identical regardless of whether the tissue exhibits long-term impedance or not. Since long-term impedance changes, relative to the short-term impedance changes, are slow, and occur over a long period of time, its effects are only reflected in adjustments made to the compliance voltage margin and/or compliance voltage adjustment intervals in the third period after the effects of the rapidly fluctuating short-term impedance have subsided. Exemplary techniques of adjusting the compliance voltage margin and/or compliance voltage adjustment interval will be discussed below.

In the preferred embodiment, the DBS system 10 dynamically adjusts the compliance voltage margin and/or the compliance voltage adjustment interval based on electrical parameter data indicative of tissue impedance that is measured at compliance voltage adjustment intervals. Measuring electrical parameter data related to tissue impedance allows a means for tracking a change in tissue impedance at every compliance voltage adjustment interval, such that the compliance voltage margin and/or compliance voltage adjustment interval may be adjusted to better suit a current and known state of tissue impedance change. This allows for precise and efficient compliance voltage adjustments such that the compliance voltage margin is only decreased and/or the compliance voltage adjustment interval is only increased at a point when the measured data indicates that a change in tissue impedance has sufficiently decreased and not any sooner than that point.

In the illustrated embodiment, the electrical parameter data that is measured by the DBS system 10 is the tissue voltage drop $V_R$. Although other voltage drops across certain components of the IPG 14 may be similarly used, as will be discussed in further detail below, the tissue voltage drop $V_R$ is the preferred electrical parameter data since changes in the tissue voltage drop $V_R$ best mirror the changes in tissue impedance, as discussed previously. Thus, for ease of illustration, the following discussion will focus on the tissue voltage drop $V_R$.

To determine how fast the tissue impedance is changing, the DBS system 10 is configured for computing a function of the tissue voltage drops $V_R$ measured at multiple compliance voltage adjustment intervals. In one embodiment, the computed function of the tissue voltage drops $V_R$ may be a difference in the tissue voltage drops $V_R$ measured at multiple compliance voltage adjustment intervals. The difference may be calculated between tissue voltage drops $V_R$ measured at consecutive compliance voltage adjustment intervals. For example, to determine the short-term rate of impedance change during the first hour of the compliance voltage calibration process, the DBS system 10 may calculate a difference in consecutive tissue voltage drops $V_R$ measured at every compliance voltage adjustment interval (e.g., 1 minute intervals during the first period or 5 minute intervals during the second period). Or the difference may be calculated between tissue voltage drops $V_R$ at any two specific compliance voltage adjustment intervals. For example, to determine the long-term rate of impedance change, the DBS system 10 may calculate a difference in tissue voltage drops $V_R$ at 24 hour intervals thereby tracking a daily change in impedance starting at the point of implantation.

In another embodiment, the computed function may be an average of the differences of measured tissue voltage drop $V_R$ at multiple compliance voltage adjustment intervals. Using an average of the differences between the tissue voltage drops $V_R$ at consecutive compliance voltage adjustment intervals (e.g., the most recent intervals) may eliminate outlier measurements, and prove to be a more reliable indicator of the change in impedance than using individual difference values. For example, to determine the short-term rate of impedance change during the first hour of the compliance voltage calibration process, the DBS system 10 may calculate art average of the three most recent differences between consecutively measured tissue voltage drops $V_R$. Similarly, to determine the long-term rate of impedance change to be used in making compliance voltage adjustments during the third period, the DBS system 10 may calculate at average of the three most recent daily-measured differences of the tissue voltage drops $V_R$.

The computed function of the multiple tissue voltage drops $V_R$ (measured at multiple compliance voltage adjustment intervals) is compared to a set of threshold values, each of which is indicative of a rate of impedance change that corresponds to a suitable compliance voltage margin and/or compliance voltage adjustment interval. Typically, the set of threshold values is in descending order such that the largest threshold value represents a more rapidly changing tissue impedance, and the smallest threshold value represents a stable tissue impedance. It should be appreciated that there may be separate threshold values indicative of short-term rates of impedance change and long-term rates of impedance change. Thus, the computed function of the tissue voltage drops $V_R$ measured at short consecutive compliance voltage adjustment intervals (short-term tissue voltage drops $V_R$) may be compared to the short-term set of threshold values indicative of short-term rates of impedance change to accordingly adjust the compliance voltage margin and/or compliance voltage adjustment interval for the first two periods of the compliance voltage calibration process. Once the short-term impedance has stabilized, the computed function of the tissue voltage drops $V_R$ measured daily (long-term tissue voltage drops $V_R$) may be compared to a long-term threshold value indicative of long-term stable impedance to accordingly adjust the compliance voltage margin and/or compliance voltage adjustment interval during the third period of the compliance voltage calibration process.

When the computed function of the tissue voltage drops $V_R$ becomes equal to or drops below one of the threshold values, the DBS system 10 automatically adjusts the compliance voltage margin and/or compliance voltage adjustment interval corresponding to that threshold value. The compliance voltage margin and/or compliance voltage adjustment interval at following compliance voltage adjustment intervals will be maintained at this adjusted compliance voltage margin and/or this adjusted compliance voltage adjustment interval until the computed function meets or falls below another threshold value that is indicative of more stable impedance.

Although not illustrated in FIG. 3, it should be appreciated that even after tissue impedance has stabilized in the months after implantation, it may increase or decrease or generally become unstable at a later time due to unforeseen circumstances (e.g., a change in position of the neuromodulation leads 12, an unforeseen change in brain tissue, etc.). In such a case, the long-term impedance curve shown in FIG. 3 may repeat itself at the later time such that the compliance voltage margin and/or compliance voltage adjustment interval are once again adjusted differently during the third period based on when (over the course of the new long-term impedance change) the compliance voltage calibration process is initiated. Thus, as a result of the increasing long-term impedance, if the computed function of the long-term tissue voltage drops $V_R$ becomes greater than the long-term threshold value indicative of stable impedance, the DBS system 10 accordingly adjusts the compliance voltage margin and/or compliance voltage adjustment interval to those appropriate for long-term unstable impedance.

Referring now to FIG. 8, one exemplary embodiment of dynamically adjusting both the compliance voltage margin and the compliance voltage adjustment interval based on both short-term and long-term tissue voltage drops $V_R$ is illustrated. During Period 1 of the compliance voltage calibration process (compliance voltage margin adjustments of 10% made at compliance voltage adjustment intervals of 1 minute), the difference between short-term tissue voltage drops $V_R$ is greater than Short-term Threshold Value 1. When the difference between short-term tissue voltage drops $V_R$ meets or drops below Short-term Threshold Value 1, the DBS system 10 automatically switches from Period 1 to Period 2. During Period 2 (compliance voltage margin adjustments of 5% made at compliance voltage adjustment intervals of 5 minutes), the difference between short-term tissue voltage drops $V_R$ remains equal to or less than Short-term Threshold Value 1, but greater than Short-term Threshold Value 2. When the difference between short-term tissue voltage drops $V_R$ meets or drops below Short-term Threshold Value 2, the DBS system 10 switches from Period 2 to either Period 3a or Period 3b based on long-term stability of tissue impedance.

In particular, when the difference between the short-term tissue voltage drops $V_R$ meets or drops below Short-term Threshold Value 2, but the difference between long-term tissue voltage drops $V_R$ is greater than Long-term Threshold Value 1, the DBS system 10 automatically switches from Period 2 to Period 3a. During Period 3a (compliance voltage margin adjustments of 3% made at compliance voltage adjustment intervals of 4 hours), the difference between the short-term tissue voltage drops $V_R$ remains equal to or less than Short-term Threshold Value 2, and the difference between long-term tissue voltage drops $V_R$ remains greater than Long-term Threshold Value 1.

In contrast, when the difference between the short-term tissue voltage drops $V_R$ meets or drops below Short-term Threshold Value 2, and the difference between long-term tissue voltage drops $V_R$ meets or drops below Long-term Threshold Value 1, the DBS system 10 automatically switches from Period 2 to Period 3b. During Period 3b (compliance voltage margin adjustments of 2% made at compliance voltage adjustment intervals of 24 hours), the difference between the short-term tissue voltage drops $V_R$ remains equal to or less than Short-term Threshold Value 2, and the difference between long-term tissue voltage drops $V_R$ remains equal to or less than Long-term Threshold Value 1.

In an alternate embodiment, instead of dynamically adjusting the compliance voltage margin and/or the compliance voltage adjustment intervals based on electrical parameter data measured at prior compliance voltage adjustments, the compliance voltage margin and/or compliance voltage adjustment intervals may be automatically adjusted based on a predetermined time schedule. The predetermined time schedule may be designed based on empirical studies performed on previous patients. Although this embodiment may not follow tissue impedance as closely as the preferred embodiment does, as described above, it may be more energy-efficient because energy is not used in measuring electrical parameter data to determine when to adjust the compliance voltage margin and/or compliance voltage adjustment interval.

For example, still referring to FIG. 8, to compensate for short-term impedance, instead of requiring the difference in tissue voltage drops $V_R$ to reach a particular threshold value before switching periods, the DBS system 10 may automatically switch from Period 1 to Period 2 after the first 20 minutes of the compliance voltage calibration process. After another 40 minutes have elapsed, the DBS system 10 may then automatically switch from Period 2 to either Period 3*a* or Period 3*b* depending on when the neuromodulation leads 12 were implanted into the tissue.

To compensate for long-term impedance during the third period, after the short-term impedance has stabilized, instead of tracking the daily change of impedance to determine whether the long-term impedance has stabilized, the DBS system 10 may automatically adjust the compliance voltage margin and/or the compliance voltage adjustment interval differently after a predetermined time (e.g., 5 weeks) after implantation has elapsed. For example, at compliance voltage calibration processes initiated during the first five weeks after implantation, the DBS system 10 may automatically switch from Period 2 to Period 3*a* after the 40 minutes of Period 2 have elapsed. Period 3*a* is then maintained until the IPG is turned off or a new compliance voltage calibration process is initiated. Similarly, at compliance voltage calibration processes initiated any time after the first five weeks of implantation, the DBS system 10 may automatically switch from Period 2 to Period 3*b* after the 40 minutes of Period 2 have elapsed. Period 3*b* is similarly maintained until the IPG is turned off or a new compliance voltage calibration process is initiated. It should be appreciated that the predetermined time schedule may be programmed by the user and may be modified to better suit the long-term and short-term changes in tissue impedance.

Although the compliance voltage margin and compliance voltage adjustment interval are illustrated as being adjusted together in the foregoing example, it should be appreciated that the compliance voltage margin and the compliance voltage interval may be adjusted independently of the other. For example, if the compliance voltage calibration process is initiated when the tissue impedance is declining steadily but has not stabilized completely (e.g., week 4-15 in FIG. 3), the compliance voltage margin may be decreased from 3% to 2%, but the compliance voltage adjustment interval may remain at 4 hours. Or, in another example, when the tissue impedance is declining steadily during the second period of the compliance voltage calibration process (e.g., minutes 20-60 in FIG. 4), the compliance voltage margin may be decreased from 5% to 3%, but the compliance voltage adjustment interval may remain at 5 minutes.

Figure 9:
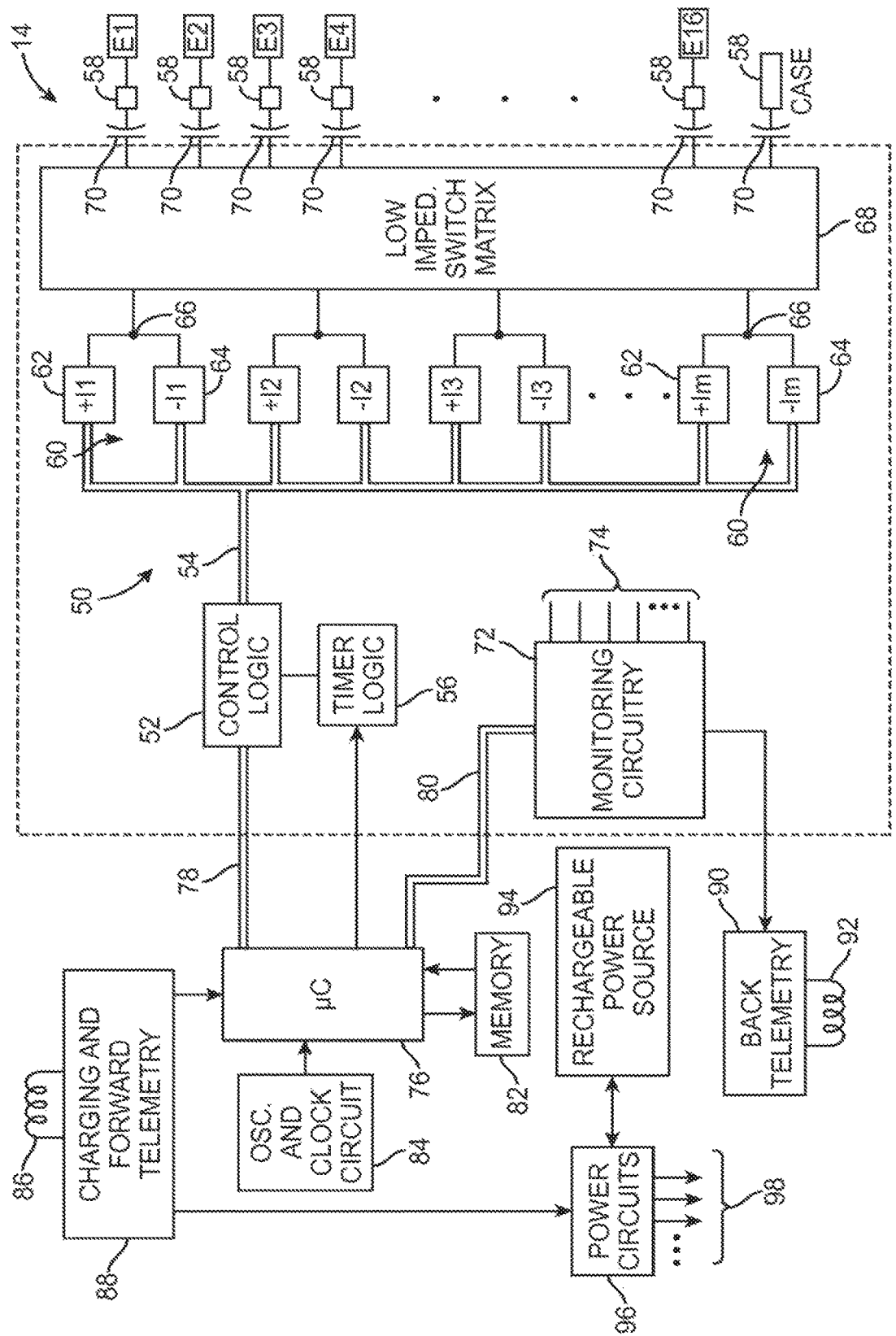
FIG. 9 is a block diagram of the internal components of the IPG of FIG. 6.

Turning next to FIG. 9, the main internal components of the IPG 14 will now be described. The IPG 14 includes analog output circuitry 50 configured for generating electrical stimulation energy in accordance with a defined pulsed waveform having a specified pulse amplitude, pulse rate, pulse duration, and pulse shape under control of control logic 52 over data bus 54. Control of the pulse rate and pulse duration of the electrical waveform is facilitated by timer logic circuitry 56, which may have a suitable resolution, e.g., 10 µs. The electrical stimulation energy generated by the analog output circuitry 50 is output to electrical terminals 58 corresponding to electrodes E1-E16 and $E_{case}$.

The analog output circuitry 50 may either comprise one or more independently controlled electrical sources, which take the form of current sources and/or current sinks, for providing stimulation pulses of a specified and known amperage to or from the electrodes 26, or voltage sources and/or voltage sinks for providing stimulation pulses of a specified and known voltage at the electrodes 26. The current (or voltage) sources or sinks include constant current (or voltage) sources and associated analog switches to generate the electrical pulse trains.

For example, in the illustrated embodiment, the analog output circuitry 50 comprises a plurality m independent current source/sink pairs 60 conveying electrical stimulation energy between the electrical terminals 58 at a specified and known amperage. Each pair 60 includes a current source 62 that functions as a positive (+) or anodic current source (e.g., a PDAC), and a current sink 64 that functions as a negative (−) or cathodic current sink (e.g., an NDAC). The outputs of the anodic current source 62 and the cathodic current sink 64 of each pair 60 are connected to a common node 66.

In essence, each current source/sink pair 60 takes the form of a reconfigurable current source whose polarity can be switched. That is, by activating the anodic current source 62 and deactivating the cathodic current sink 64, the current source/sink pair 60 can be configured as an anodic current source, and by deactivating the anodic current source 62 and activating the cathodic current sink 64, the current source/sink pair 60 can be configured as a cathodic current sink. The current source 62 and current sink 64 may, e.g., take the form of the current source 1 and current sink 2 illustrated in FIG. 1.

The analog output circuitry 50 further comprises a low impedance switching matrix 68 through which the common node 66 of each current source/sink pair 60 is connected to any of the electrical terminals 58, and a capacitor 70 coupled between each electrode 26 and the switching matrix 68. Thus, for example, it is possible to program the first anodic current source 62 (+I1) to produce a pulse having a peak amplitude of +4 mA (at a specified rate and for a specified duration), and to synchronously program the second cathodic current sink 64 (−I2) to similarly produce a pulse having a peak amplitude of −4 mA (at the same rate and pulse duration), and then connect the node 66 of the anodic current source 62 (+I1) to the electrical terminal 68 corresponding to electrode E3, and connect the node 66 of the cathodic current sink 64 (−I2) to the electrical terminal 68 corresponding to electrode E1.

Hence, it is seen that each of the programmable electrical terminals 58 can be programmed to have a positive (sourcing current), a negative ((sinking current), or off (no current) polarity. Further, the amplitude of the current pulse being sourced or sunk to or from a given electrode may be programmed to one of several discrete current levels, e.g., between 0 to 10 mA in steps of 100 μA, within the output voltage/current requirements of the IPG 14. Additionally, in one embodiment, the total current output by a group of electrical terminals 58 can be up to ±20 mA (distributed among the electrodes included in the group). Also, the pulse duration of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 5000 pulses per second (pps). Other programmable features can include slow start/end ramping, burst stimulation cycling (on for X time, off for Y time), interphase (i.e., the duration between first and second phases of biphasic energy), and open or closed loop sensing modes. Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IPG 14 is configured as an anode (positive).

It can be appreciated that an electrical terminal 58 may be assigned an amplitude and included with any of up to k possible groups, where k is an integer corresponding to the number of channels, and in one embodiment, is equal to 4, and with each channel k having a defined pulse amplitude, pulse duration, pulse rate, and pulse shape. Other channels may be realized in a similar manner. Thus, each channel identifies which electrical terminals 58 (and thus electrodes) are selected to synchronously source or sink current, the pulse amplitude at each of these electrical terminals, and the pulse duration, pulse rate, and pulse shape. The individual electrical pulse trains that are concurrently generated to create the combined electrical pulse train can be respectively conveyed in the k number of channels. Amplitudes and polarities of electrodes on a channel may vary, e.g., as controlled by the RC 16. External programming software in the CP 18 is typically used to set stimulation parameters including electrode polarity, amplitude, pulse rate and pulse duration for the electrodes of a given channel, among other possible programmable features.

Further details discussing this type of current source architecture is described in U.S. Pat. No. 6,181,996, which has previously been incorporated by reference. Of course, other types of current source architectures, such as the dedicated current source architecture described in U.S. Pat. No. 6,516,227 or the distributed current source architecture described in U.S. patent application Ser. No. 11/177,503, which have been previously incorporated herein by reference, can alternatively be used.

The IPG 14 further comprises monitoring circuitry 72 for monitoring the status of various nodes or other points 74 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Thus, the monitoring circuitry 72 is configured for taking such electrical measurements (e.g., current output magnitude, electrode impedance, field potential, evoked action potentials, etc.) for performing such functions as detecting fault conditions between the electrodes 26 and the analog output circuitry 50, determining the coupling efficiency between the electrodes 26 and the tissue, facilitating lead migration detection, etc. More significant to the present inventions, the monitoring circuitry 72 is configured for measuring voltage drops across all of the current sources 62, current sinks 64, and capacitors C1-C16.

The IPG 14 further comprises processing circuitry in the form of a microcontroller (μC) 76 that controls the control logic over data bus 78, and obtains status data from the monitoring circuitry 72 via data bus 80. The IPG 14 additionally controls the timer logic 56 and switching matrix 68. The IPG 14 further comprises memory 82 and oscillator and clock circuitry 84 coupled to the microcontroller 76. The microcontroller 76, in combination with the memory 82 and oscillator and clock circuit 84, thus comprise a microprocessor system that carries out a program function in accordance with a suitable program stored in the memory 82. Alternatively, for some applications, the function provided by the microprocessor system may be carried out by a suitable state machine. The memory 82 also stores the threshold values, and optionally the compliance voltage adjustment time schedule, discussed above with respect to the adjustment of the compliance voltage adjustment interval and compliance voltage margin.

Thus, the microcontroller 76 generates the necessary control and status signals, which allow the microcontroller 76 to control the operation of the IPG 14 in accordance with a selected operating program and stimulation parameters. In controlling the operation of the IPG 14, the microcontroller 76 is able to individually generate the individual electrical pulse trains at the electrodes 26 using the analog output circuitry 50, in combination with the control logic 52 and timer logic 56, thereby activating selected ones of the electrodes 26, including the monopolar case electrode. In accordance with stimulation parameters stored within the memory 82, the microcontroller 76 may control the polarity, amplitude, rate, pulse duration and channel through which the current stimulation pulses are provided. The microcontroller 76 also facilitates the storage of electrical parameter data (or other parameter data) measured by the monitoring circuitry 72 within memory 82, and also provides any computational capability needed to analyze the raw electrical parameter data obtained from the monitoring circuitry 72 and compute numerical values from such raw electrical parameter data. More significant to the present inventions, the microcontroller 76 is capable of adjusting the compliance voltage supplied to the analog output circuitry 50 in accordance with the compliance voltage calibration discussed above.

The IPG 14 further comprises an alternating current (AC) receiving coil 86 for receiving programming data (e.g., the operating program and/or stimulation parameters) from the RC 16 and/or CP 18 (shown in FIG. 5) in an appropriate modulated carrier signal, and charging and forward telemetry circuitry 88 for demodulating the carrier signal it receives through the AC receiving coil 86 to recover the programming data, which programming data is then stored within the memory 82, or within other memory elements (not shown) distributed throughout the IPG 14.

The IPG 14 further comprises back telemetry circuitry 90 and an alternating current (AC) transmission coil 92 for sending informational data sensed through the monitoring circuitry 72 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. The back telemetry features allow raw or processed electrical parameter data (or other parameter data) previously stored in the memory 82 to be downloaded from the IPG 14 to the RC 16 and/or CP 18.

The IPG 14 further comprises a rechargeable power source 94 and power circuits 96 for providing the operating power to the IPG 14. The rechargeable power source 94 may, e.g., comprise a lithium-ion or lithium-ion polymer battery. The rechargeable battery 94 provides an unregulated voltage to the power circuits 96. The power circuits 96, in turn, generate the various voltages 98, some of which are regulated and some of which are not, as needed by the various circuits located within the IPG 14. Significantly, the power circuits 96 include a voltage regulator (discussed in further detail below) that supplies the compliance voltage to the analog output circuitry 50. The rechargeable power source 94 is recharged using rectified AC power (or DC power converted from AC power through other means, e.g., efficient AC-to-DC converter circuits, also known as "inverter circuits") received by the AC receiving coil 86. To recharge the power source 94, the external charger 22 (shown in FIG. 1), which generates the AC magnetic field, is placed against, or otherwise adjacent, to the patient's skin over the implanted IPG 14. The AC magnetic field emitted by the external charger induces AC currents in the AC receiving coil 86. The charging and forward telemetry circuitry 88 rectifies the AC current to produce DC current, which is used to charge the power source 94. While the AC receiving coil 86 is described as being used for both wirelessly receiving communications (e.g., programming and control data) and charging energy from the external device, it should be appreciated that the AC receiving coil 86 can be arranged as a dedicated charging coil, while another coil can be used for bi-directional telemetry.

It should be noted that the diagram of FIG. 9 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No, 2003/0139781, and U.S. patent application Ser. No. 11/138,632, entitled "Low Power Loss Current Digital-to-Analog Converter Used in an Implantable Pulse Source," which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

With the basic architecture of the IPG 14 understood, the specific circuitry involved with adjusting the compliance voltage V+ supplied to the analog output circuitry 50 will now be discussed with reference to FIG. 10. As there shown, a circuit is created that includes the compliance voltage V+, a current source 62, a current sink 64, an electrode or electrodes $E_x$, capacitor(s) $C_x$ corresponding to the electrode(s) $E_x$, an electrode or electrodes $E_y$, capacitor(s) $C_y$ corresponding to the electrode(s) $E_y$, and the load resistance of the tissue $R_x$. Due to the flow of the electrical current $I_{out}$, voltage drops $V_x$ and $V_{cy}$ will be respectively generated across the current source 62 and the coupling capacitor(s) $C_x$. Similarly, due to the flow of the electrical current $I_{in}$, voltage drops $V_y$ and $V_{cy}$ will be respectively generated across the current sink 64 and the coupling capacitor(s) $C_y$. Due to the flow of the electrical currents $I_{out}$, $I_{in}$, in combination with any currents generated by other active current sources 62/sinks 64, a voltage drop $V_R$ is generated across the tissue resistance R. Of course, if only one current source 62 and only one current sink 64 are active, $I_{out}$ will be equal to $I_{in}$, and therefore, the entire voltage drop $V_R$ across the tissue resistance R will be caused by the electrical current $I_{out}/I_{in}$.

As noted earlier, the compliance voltage V+ can be set to various values while still exhibiting satisfactory current sourcing/sinking performance. Thus, the current sources involved in stimulation of tissue can be powered by a compliance voltage V+ ranging from a minimum value (below which current will be too low) to any maximum value that the voltage regulator of the power circuits 96 is capable of providing. Within this range, the stimulation current desired by a particular therapeutic regimen can be provided. However, as previously discussed, while the compliance voltage V+ can vary over a range of values while exhibiting satisfactory voltage, power is needlessly lost should the compliance voltage V+ be set to a value that is too high.

To this end, the monitoring circuitry 72 measures the voltage across (at least) the output of the current sources 62 and current sinks 64 involved in sinking and sourcing the electrical stimulation current. In the illustrated embodiment, the monitoring circuitry 72 comprises a compliance voltage sensing control circuitry 102, a switching matrix 104, and at least one voltage sensor 106. Lines 108 associated with the electrodes 26 feed into the switching matrix 104. In the given architecture illustrated in FIG. 10, more than one current source 62 or more than one current sink 64 may contribute to the current at a particular electrode. However, for ease of illustration, only one current source 60 and only one current sink 62 are shown and described.

Given their tap points, the voltage present on the lines 108 is indicative of the output voltage of the current source 60 and current sink 64, and can thus, be used to sense the output voltage of these components. The output voltage across the current source 62 at electrode or electrode $E_x$ equals the difference between the compliance voltage V+ measured at line $L_{V+}$ and the voltage measured at line $L_x$. The output voltage across the current sink 64 at electrode $E_y$ equals the difference between the voltage measured at line $L_y$ and the voltage measured at ground $L_{GND}$. The voltages on the lines 108 are provided to the switching matrix 104. As noted above, while only four lines 108 are shown for each of illustration in FIG. 10, many more lines would be present, depending on the number of electrodes 26 present. The switching matrix 104 is used to select the voltage on one line 108 and present it to the voltage sensor 106 as either $L_1$ or $L_2$ or select two voltage on two lines 108 and present them to the voltage sensor 106 as $L_1$ and $L_2$ for difference voltage calculations by the voltage sensor 106. As can be seen, the current source 62, current sink 64, switching matrix 104, and voltage sensor 106 are all controlled by the compliance voltage sensing control circuitry 102 via busses 112, 114, and 116.

Ultimately, the compliance voltage sensing circuitry 102 receives control signals from the microcontroller 76, which informs the monitoring circuitry 72 when and how the various measurements are to be made consistent with the compliance voltage adjustment calibration process described above. The voltage sensor 106 outputs an analog output voltage "Out" to the microcontroller 76, which contains an analog-to-digital (A/D) interface 110. This allows the microcontroller 76 to understand and digitally process the output voltage Out to determine the sensed voltage drops across the current source 62 or current sink 64.

Figure 10:
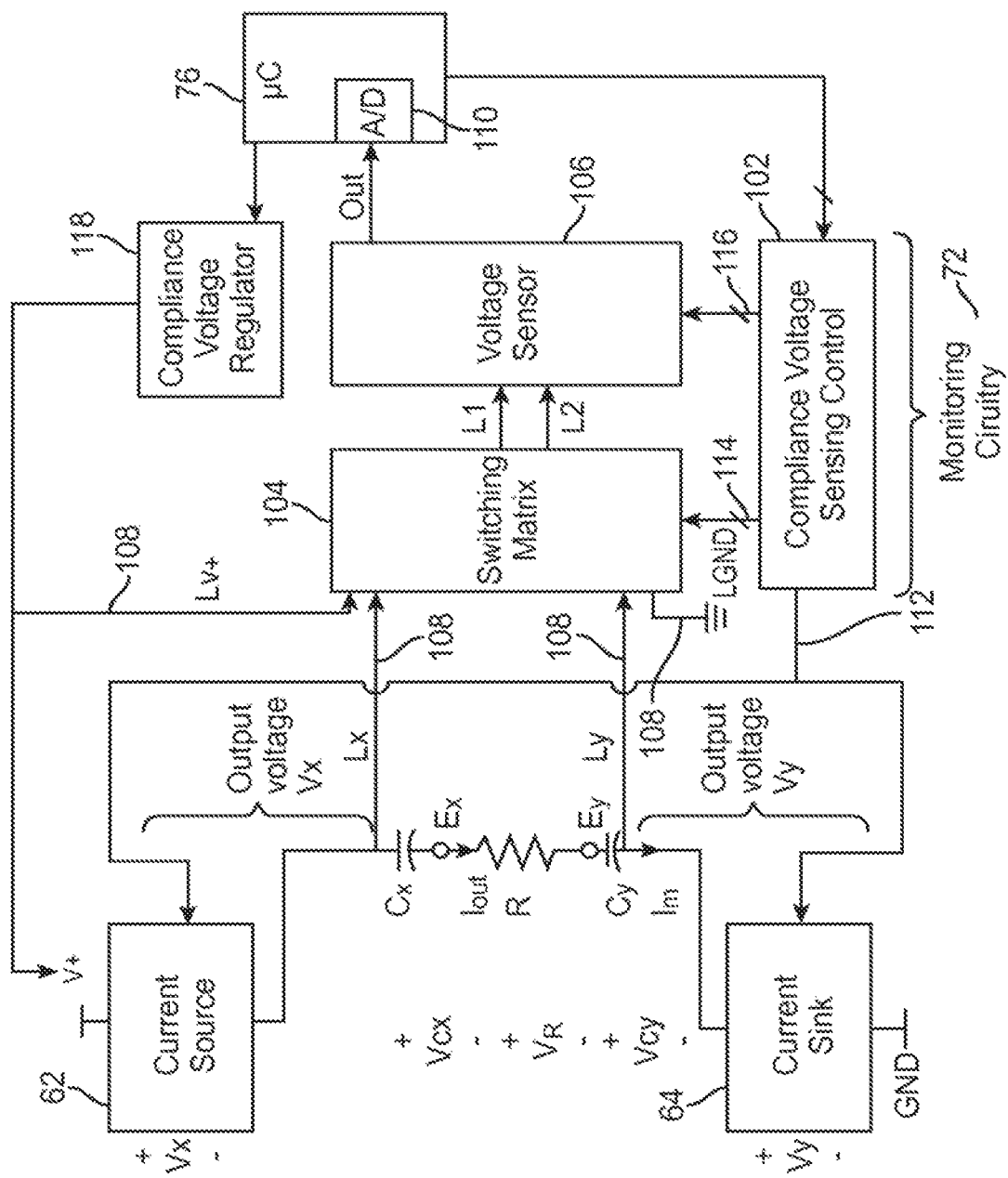
FIG. 10 is a block diagram illustrating current source/sink circuitry used in the IPG of FIG. 9.

Further details discussing the monitoring circuitry 72 illustrated in FIG. 10 are discussed in U.S. Pat. No. 8,175,719, which is expressly incorporated herein by reference. Based on the baseline compliance voltages determined over a period of time, the microcontroller 76 may adjust the compliance voltage, compliance voltage margin, and/or compliance voltage sensing interval in the manner described above.

With knowledge of these sensed voltages, the microcontroller 76 may send control signals to a voltage regulator 118 (i.e., the circuitry that ultimately adjusts the compliance voltage V+) in accordance with the compliance voltage adjustment calibration process.

In the illustrated embodiment, the microcontroller 76 computes the adjusted compliance voltage based on a voltage drop across the tissue between the electrode(s) $E_x$ associated with selected one of the current sources 62 and the electrode(s) $E_y$ associated with a selected one of the current sinks 64. Preferably, the current source 62 and current sink 64 that are selected are the worst-case current source 62 and current sink 64 (i.e., the active current source 62 with the lowest voltage drop relative to the other active current sources 62, and the active current sink 64 with the lowest voltage drop relative to the other active current sinks 64). As such, it can be ensured that the adjusted compliance voltage will be sufficient for all of the current sources 62/current sinks 64.

The microcontroller 76 can determine the voltage drop $V_R$ across the tissue resistance R by computing the difference between the known compliance voltage V+ and the sum of the measured voltage drops $V_x$, $V_y$ across the current source 62 and current sink 64 and the known voltage drops $V_{cx}$, $V_{cy}$ across the coupling capacitors $C_x$, $C_y$ (which can be obtained using Ohms' Law from the known currents $I_{out}$, $I_{in}$ and the values of the capacitors $C_x$, $C_y$). That is, $V_R = V + -(V_x + V_y + V_{cx} + V_{cy})$. Knowing the voltage drop $V_R$ across the tissue resistance R, the microcontroller 76 can then compute the adjusted compliance voltage as a function of the voltage drop $V_R$ across tissue resistance R, the desired operating voltages of the current source 62 and current sink 64, the expected voltage drops $V_{cx}$, $V_{cy}$ across the coupling capacitors $C_x$, $C_y$, and the compliance voltage margin.

If the compliance voltage margin takes the form of a percentage, microcontroller 76 can apply the compliance voltage margin to the voltage drop $V_R$ across the tissue resistance R by computing the product of $V_R$ and the compliance voltage margin, and then computing the adjusted compliance voltage as the sum of this product, the tissue voltage drop $V_R$, the capacitor voltage $V_{cx}$, $V_{cy}$, and the desired operating voltage of the current source 62 and current sink 64 to arrive at the adjusted compliance voltage V+. If the compliance voltage margin takes the form of an absolute value, the microcontroller 76 simply computes the adjusted compliance voltage as the sum of the compliance voltage margin, the tissue voltage drop $V_R$, the capacitor voltage $V_{cx}$, $V_{cy}$, and the desired operating voltage of the current source 62 and current sink 64.

In an alternative embodiment, the microcontroller 76 determines the baseline compliance voltage by directing the voltage regulator 118 to incrementally decrease the compliance voltage until the measured voltage drop across the current source 62 and current sink 64 meets a threshold value. In the illustrated embodiment, the compliance voltage is decreased from a maximum value, and the threshold value is sum of the operating voltages of the current source 62 and current sink 64, such as the saturation voltages. This alternative technique is described in U.S. Pat. No. 8,175,719, which is expressly incorporated herein by reference.

As discussed above, the microcontroller 76 is also configured for adjusting the compliance voltage adjustment interval and compliance voltage margin. These two parameters can be adjusted either in unison or independently from each other. As briefly discussed above, the microcontroller 76 may adjust either or both of the compliance voltage adjustment interval and compliance voltage margin by comparing a function (e.g., the difference between two voltage drops determined at two consecutive compliance voltage adjustment intervals, or an average of the voltage drop differences determined between a plurality of consecutive voltage adjustment intervals) of voltage drops across an element of the circuit illustrated in FIG. 10 and one or more threshold values stored in the memory 82. In the preferred embodiment, the voltage drop that dictates the adjustment of the compliance voltage adjustment interval and compliance voltage margin is the voltage drop $V_R$ across the tissue resistance R, since the voltage drop $V_R$ may be more directly correlated to impedance changes in the tissue, and thus, provides a more accurate indication of when the compliance voltage adjustment interval and compliance voltage margin should be adjusted. As such, the voltage drop on which these adjustments are based is preferably the tissue voltage $V_R$. Of course, the voltage drop on which these adjustments are based may be the compliance voltage V+, which would represent a more conservative approach to the adjustment of the compliance voltage adjustment interval and the compliance voltage margin.

Figure 11A:
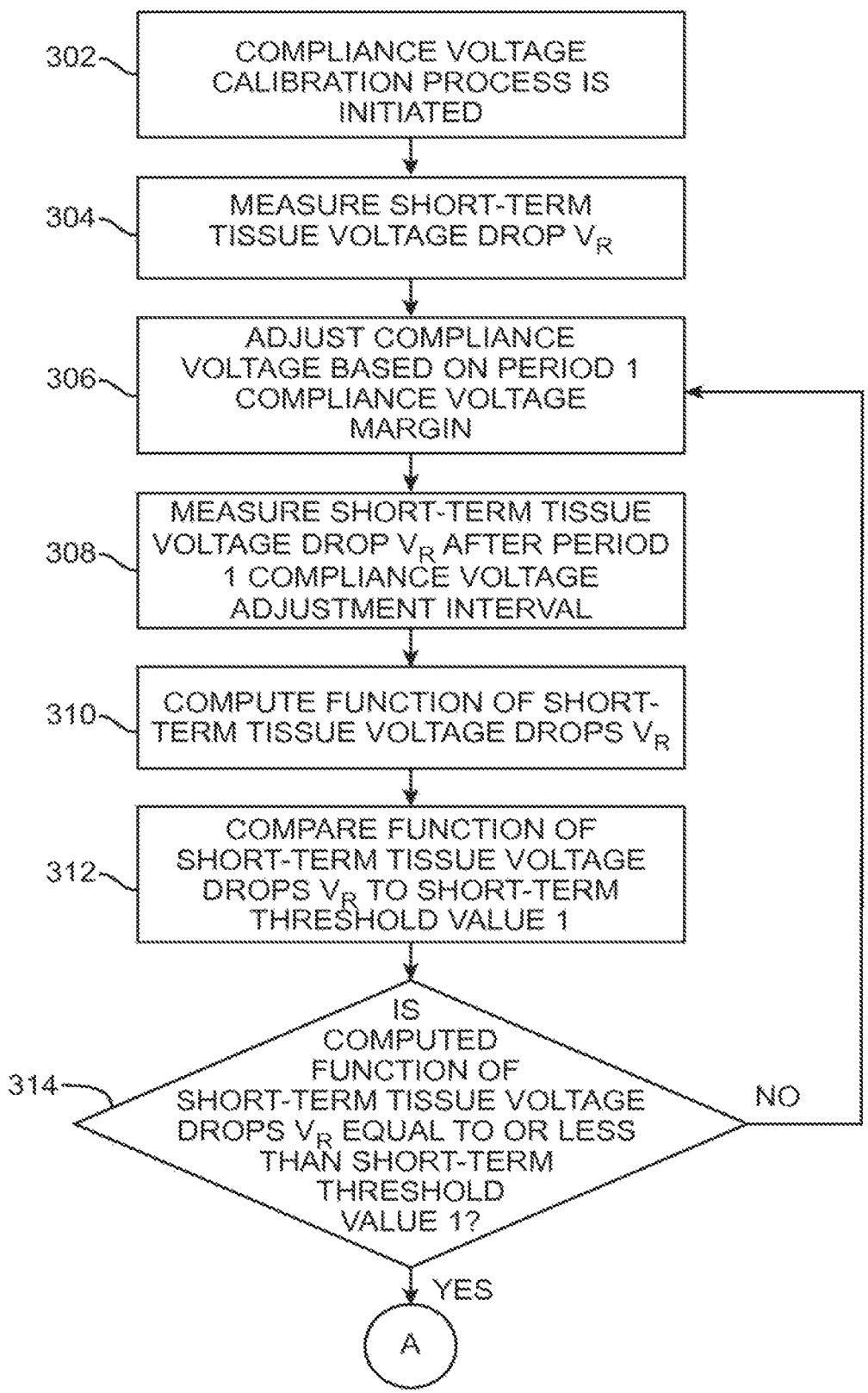
FIG. 11a-c is a flow diagram illustrating one method performed by the IPG of FIG. 6 to periodically adjust the compliance voltage over time.
Figure 11B:
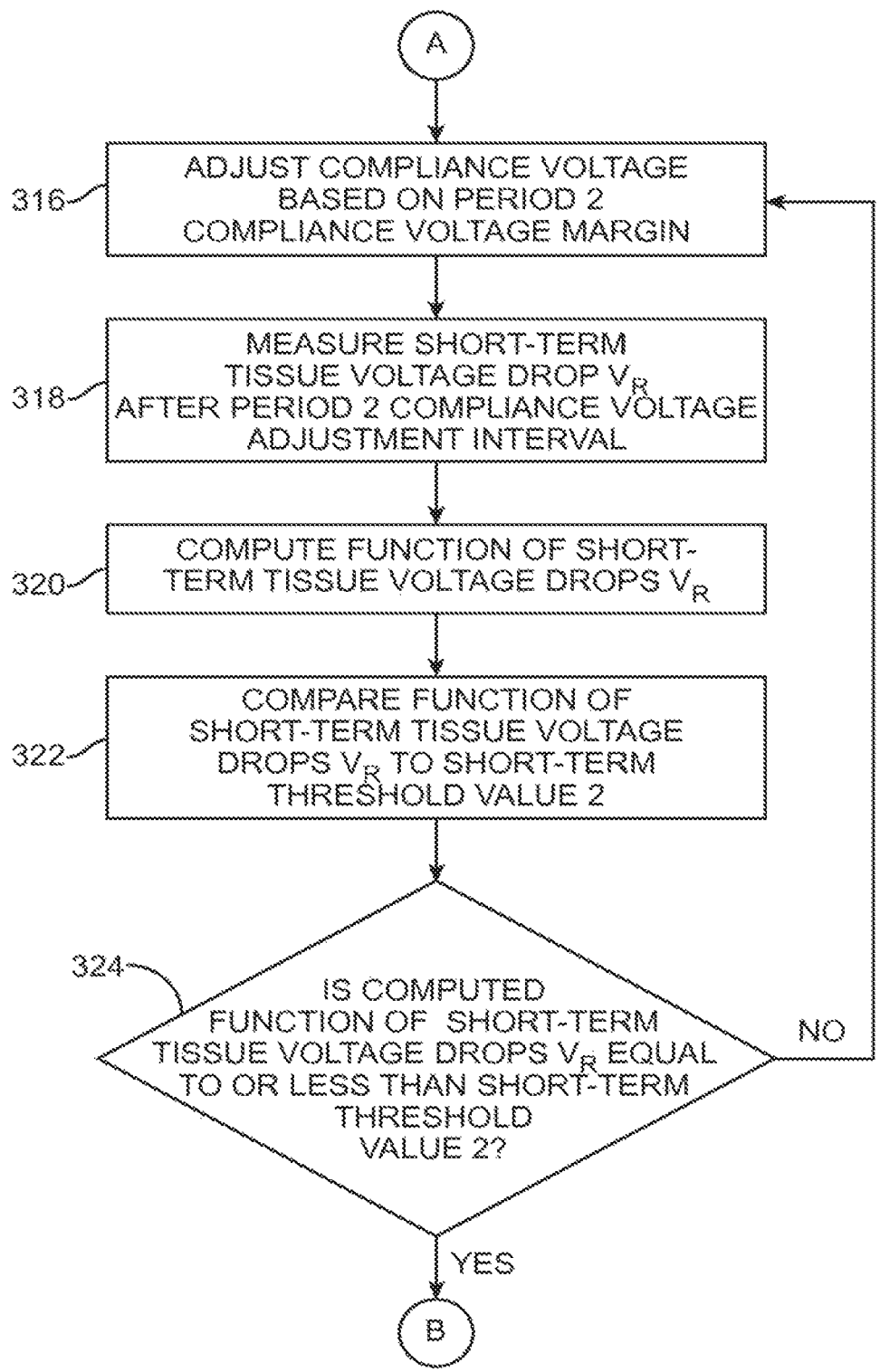
Figure 11C:
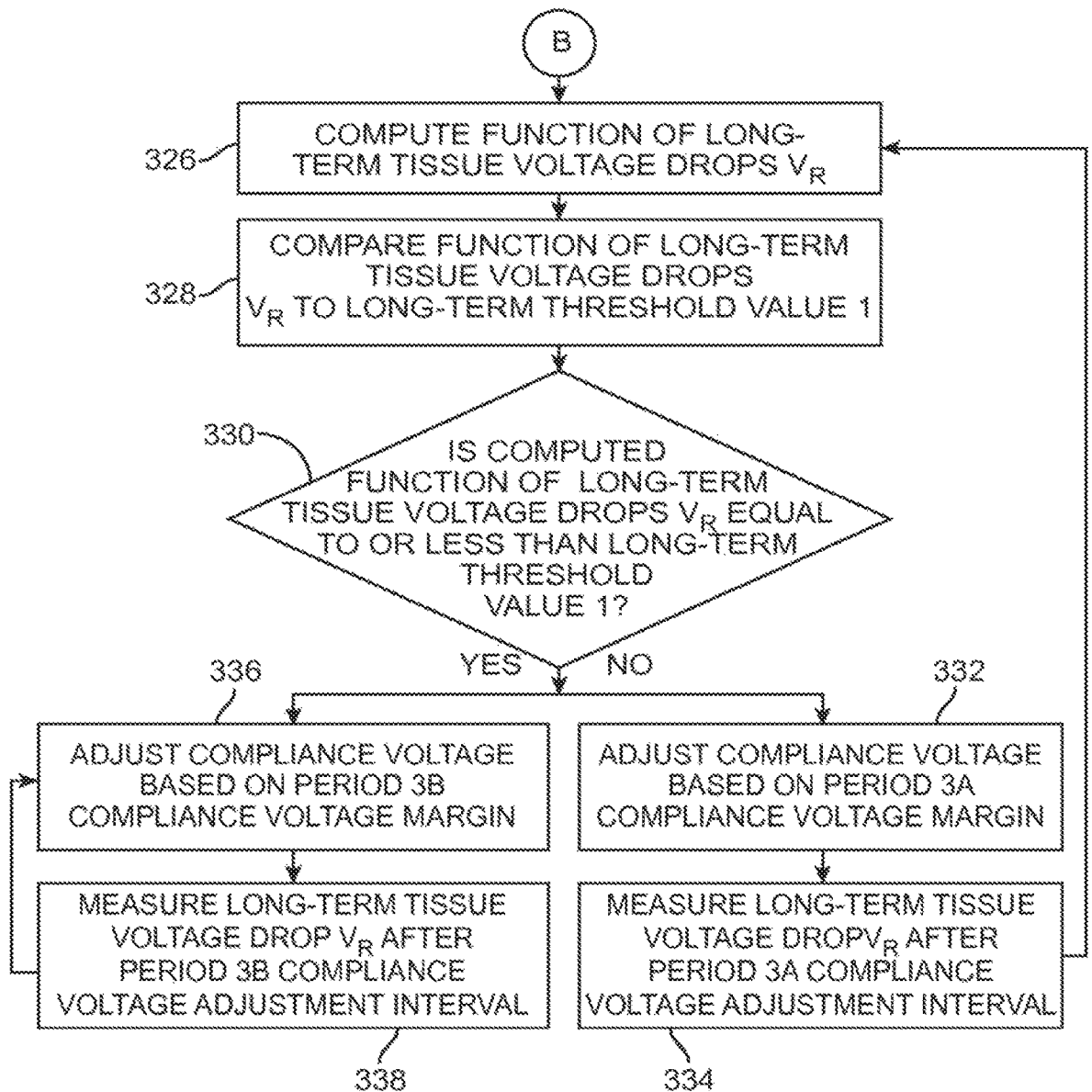

Turning now to FIG. 11, an exemplary method 300 for automatically making periodic adjustments to the compliance voltage using the DBS system 10 will now be described. For illustrative purposes, specific parameters of the compliance voltage calibration process discussed below will refer back to those of FIG. 8. First, the compliance voltage calibration process is initiated (step 302). As previously described, the compliance voltage calibration process is initiated whenever the IPG 14 is turned on or electrical energy having a new set of modulation parameters is delivered to the tissue.

Next, the DBS system 10 measures a tissue voltage drop $V_R$ across the tissue resistance R caused by the delivered electrical energy at the start of the compliance voltage calibration process (step 304).

Next, the DBS system 10 adjusts the compliance voltage based on a high compliance voltage margin typical for Period 1 (e.g., 10%) (step 306). As described previously, the DBS system 10 adjusts the compliance voltage as a function of the compliance voltage margin (e.g., a percentage of one or more voltage drops in the IPG 14 or a fixed margin) on top of a baseline compliance voltage necessary to deliver the programmed electrical energy.

Next, the DBS system 10 measures the short-term tissue voltage drop $V_R$ again after a short compliance voltage adjustment interval associated with Period 1 (e.g., 1 minute) has elapsed (step 308). As discussed above, the short-term tissue voltage drops $V_R$, in the illustrated embodiment, refer to tissue voltage drops $V_R$ measured after every compliance voltage adjustment interval.

Next, to determine how fast the short-term impedance is changing, the DBS system 10 computes a function of the short-term tissue voltage drops $V_R$ (step 310). As described previously, the computed function may be a difference between two consecutively measured tissue voltage drops $V_R$ or an average of the differences between recently-measured consecutive tissue voltage drops $V_R$.

Next, the DBS system 10 compares the computed function of the short-term tissue voltage drops $V_R$ to Short-term Threshold Value 1 (step 312). If the computed function is greater than Short-term Threshold Value 1 (step 314), the DBS system 10 returns to adjusting the compliance voltage based on the high compliance voltage margin associated with Period 1 (step 306).

If the computed function of the short-term tissue voltage drops $V_R$ is equal to or less than Short-term Threshold Value 1 (step 314), the DBS system 10 adjusts the compliance voltage based on a moderate compliance voltage margin typical for Period 2 (e.g., 5%) (step 316). Next, similar to the above-mentioned steps for Period 1, the DBS system 10 measures the short-term tissue voltage drop $V_R$ after a moderate compliance voltage adjustment interval (e.g., 5 minutes) associated with Period 2 has elapsed (step 318), and computes a function of the short-term tissue voltage drops $V_R$ (step 320). Next, the DBS system 10 compares the computed function of the short-term tissue voltage drops $V_R$ to Short-term Threshold Value 2 of the set of short-term threshold values (step 322).

Again, similar to the above-mentioned steps for Period 1, if the computed function of the short-term tissue voltage drops $V_R$ is greater than Short-term Threshold Value 2 (step 324), the DBS system 10 returns to adjusting the compliance voltage based on the moderate compliance voltage margin associated with Period 2 (step 316).

If the computed function of the short-term tissue voltage drops $V_R$ is equal to or less than Short-term Threshold Value 2 (step 326), the DBS system 10 computes a function of long-term tissue voltage drops $V_R$. As described previously, the long-term tissue voltage drops, in the illustrated embodiment, refer to tissue voltage drops $V_R$ measured daily from the point of implantation to track a long-term change in tissue impedance. As was the case with short-term tissue voltage drops $V_R$, the computed function may be a difference between two consecutively measured daily tissue voltage drops $V_R$ or an average of the differences between the most recently measured consecutive daily tissue voltage drops $V_R$.

Next, to determine how fast the long-term impedance is changing, the DBS system 10 compares the computed function of the long-term tissue voltage drops $V_R$ to Long-term Threshold Value 1 (step 328). If the computed function of the long-term tissue voltage drops $V_R$ is greater than Long-term Threshold Value 1 (step 330), the DBS system 10 adjusts the compliance voltage based on the compliance voltage margin associated with Period 3a (long-term unstable impedance) (e.g., 3%) (step 332), and measures the long-term tissue voltage drop $V_R$ after the compliance voltage adjustment interval typical for Period 3a (e.g., 4 hours) has elapsed (step 334). Next, the DBS system 10 returns to computing a function of the long-term tissue voltage drops $V_R$ (step 326) to determine the rate of change of long-term impedance, and adjusting the compliance voltage based on the stability of the long-term impedance.

If the computed function of the long-term tissue voltage drops $V_R$ is equal to or less than Long-term Threshold Value 1 (step 336), the DBS system 10 adjusts the compliance voltage based on the compliance voltage margin associated with Period 3b (long-term stable impedance) (e.g., 2%) (step 338) and measures the long-term tissue voltage drop $V_R$ after the compliance voltage adjustment interval typical for Period 3b (e.g., 24 hours) has elapsed (step 338). Since the long-term impedance has stabilized at this point, the DBS system 10 simply returns to adjusting the compliance voltage based on the compliance voltage margin typical for Period 3b after every compliance voltage adjustment interval. The DBS system 10 continues to make these periodic adjustments to the compliance voltage margin until the IPG 14 is turned off or a new compliance voltage calibration process is started.

It can be appreciated that by periodically adjusting the compliance voltage, at varying compliance voltage adjustment intervals, based on varying compliance voltage margins, the DBS system 10 automatically compensates for both short-term and long-term tissue impedance in an efficient manner. The compliance voltage calibration process ensures that the intended DBS therapy remains efficacious without unnecessarily wasting energy. Although the compliance voltage calibration process has been described with respect to DBS therapy, it should be appreciated that this calibration process can be similarly utilized to calibrate other tissue modulation systems.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for use with a plurality of electrodes implanted within tissue, the system comprising:
   output circuitry configured to deliver electrical energy to at least some of the plurality of electrodes;
   a voltage regulator configured to supply a compliance voltage to the output circuitry;
   monitoring circuitry configured to determine a rate of change in tissue impedance; and
   control/processing circuitry configured to automatically calibrate the compliance voltage for the voltage regulator at a compliance voltage adjustment interval by adjusting the compliance voltage adjustment interval and a compliance voltage margin based on the determined rate of change in tissue impedance.

2. The system of claim 1, wherein the control/processing circuitry is configured to determine the compliance voltage margin based on a voltage drop across tissue.

3. The system of claim 1, wherein the control/processing circuitry is configured to determine the compliance voltage margin based on a voltage drop across analog circuitry.

4. The system of claim 1, wherein the control/processing circuitry is configured to determine the compliance voltage margin based on at least one voltage drop generated by an implantable pulse generator.

5. The system of claim 1, wherein the control/processing circuitry is configured to maintain a first compliance voltage margin during a first time period, maintain a second compliance voltage margin during a second time period, and maintain a third compliance voltage margin during a third time period.

6. The system of claim 5, wherein the first compliance voltage is greater than the second compliance voltage and the second compliance voltage is greater than the third compliance voltage.

7. The system of claim 6, wherein the first time period is less than the second time period and the second time period is less than the third time period.

8. The system of claim 1, wherein the control/processing circuitry is configured to maintain a first compliance voltage adjustment interval during the first time period, maintain a second compliance voltage adjustment interval during the second time period, and maintain a third compliance voltage adjustment interval during the third time period.

9. The system of claim 8, wherein the first compliance voltage adjustment interval is less than the second compliance voltage adjustment interval and the second compliance voltage adjustment interval is less than the third compliance voltage adjustment interval.

10. The system of claim 1, wherein the output circuitry includes at least one of a current source and a current sink configured for delivering the therapeutic electrical energy between the electrical terminals, and the monitoring circuitry is configured for measuring the voltage drop across the at least one of the current source and the current sink.

11. The system of claim 10, wherein the control/processing circuitry is configured to determine a voltage drop across the tissue based on a difference between the compliance voltage and the measured voltage drop across the at least one of the current source and the current sink.

12. The system of claim 11, further comprising a plurality of coupling capacitors, wherein the at least one of the current source and the current sink is configured to deliver therapeutic electrical energy between the plurality of electrical terminals via the capacitors, the monitoring circuitry is configured to monitor the voltage drops across the capacitors, and the control/processing circuitry is configured to determine the voltage drop across the tissue based on a difference between the compliance voltage and a sum of the measured voltage drop across the at least one of the current source and the current sink and the measured voltage drops across the capacitors.

13. The system of claim 12, wherein the compliance voltage adjustment interval is adjusted from a value in the range of 0-20 minutes to a value in the range greater than 20 minutes, the compliance voltage margin is a voltage drop percentage, and the voltage drop percentage is adjusted from a value in the range greater than 10% to a value less than 10%.

14. The system of claim 12, wherein the compliance voltage adjustment interval is adjusted from a value in the range of 20-60 minutes to a value in the range greater than 60 minutes, the compliance voltage margin is a voltage drop percentage, and the voltage drop percentage is adjusted from a value in the range between 5%-10% to a value less than 2%.

15. The system of claim 12, wherein the compliance voltage adjustment interval is adjusted from a value in the range of 60 minutes to 1 day to a value in the range greater than 1 day the compliance voltage margin is a voltage drop percentage, and the voltage drop percentage is adjusted from a value in the range between 1%-2% to a value less than 1%.

16. A method performed using a system comprising output circuitry, a voltage regulator, monitoring circuitry, and control/processing circuitry, wherein the method comprises:
using the output circuitry to deliver electrical energy to at least some of a plurality of electrodes implanted within tissue;
using the voltage regulator to supply a compliance voltage to the output circuitry;
using the monitoring circuitry to determine a rate of change in tissue impedance; and
using the control/processing circuitry to automatically calibrate the compliance voltage for the voltage regulator at a compliance voltage adjustment interval by adjusting the compliance voltage adjustment interval and a compliance voltage margin based on the determined rate of change in tissue impedance.

17. The method of claim 16, further comprising using the control/processing circuitry to maintain a first compliance voltage margin during a first time period, maintain a second compliance voltage margin during a second time period, and maintain a third compliance voltage margin during a third time period.

18. The method of claim 16, further comprising using the control/processing circuitry to maintain a first compliance voltage adjustment interval during the first time period, maintain a second compliance voltage adjustment interval during the second time period, and maintain a third compliance voltage adjustment interval during the third time period.

19. A non-transitory machine-readable medium including instructions, which when executed by a machine within a neuromodulation system that includes output circuitry and a voltage regulator, cause the machine to:
use the output circuitry to deliver electrical energy to at least some of a plurality of electrodes implanted within tissue;
use the voltage regulator to supply a compliance voltage to the output circuitry;
determine a rate of change in tissue impedance; and
automatically calibrate the compliance voltage for the voltage regulator at a compliance voltage adjustment interval by adjusting the compliance voltage adjustment interval and a compliance voltage margin based on the determined rate of change in tissue impedance.

20. The non-transitory machine-readable medium of claim 19, wherein the compliance voltage margin is determined based on a voltage drop across tissue or a voltage drop across the output circuitry.

* * * * *